US012758902B2

(12) United States Patent
Steele et al.

(10) Patent No.: US 12,758,902 B2
(45) Date of Patent: Oct. 13, 2026

(54) ROTARY INTERFACE FOR FLUID ASSEMBLIES AND RELATED METHODS OF FABRICATION AND USE

(71) Applicant: Mott Corporation, Farmington, CT (US)

(72) Inventors: James K. Steele, Middlefield, CT (US); Allen Beaune, Norfolk, CT (US); Matthew Siok, Farmington, CT (US); Aravind Mohanram, Avon, CT (US); Alex Hill, South Windsor, CT (US); Phillip Armstrong, Farmington, CT (US)

(73) Assignee: MOTT CORPORATION, Farmington, CT (US)

( * ) Notice: Subject to any disclaimer, the term of this patent is extended or adjusted under 35 U.S.C. 154(b) by 1057 days.

(21) Appl. No.: 17/836,189

(22) Filed: Jun. 9, 2022

(65) Prior Publication Data

US 2022/0401858 A1 Dec. 22, 2022

Related U.S. Application Data

(60) Provisional application No. 63/208,897, filed on Jun. 9, 2021.

(51) Int. Cl.
*B01D 33/15* (2006.01)
*B01D 33/37* (2006.01)
(Continued)

(52) U.S. Cl.
CPC ............ *B01D 33/15* (2013.01); *B01D 33/37* (2013.01); *B01D 33/742* (2013.01);
(Continued)

(58) Field of Classification Search
None
See application file for complete search history.

(56) References Cited

U.S. PATENT DOCUMENTS 2,928,665 A 3/1960 Epprecht
3,776,531 A 12/1973 Ebner et al.
(Continued)

FOREIGN PATENT DOCUMENTS

CN 101721921 A 6/2010
CN 203890342 U 10/2014
(Continued)

OTHER PUBLICATIONS

Bielser et al.; "Perfusion mammalian cell culture for recombinant protein manufacturing—A critical review"; Biotechnology Advances, vol. 36, No. 4; 2018; pp. 1328-1340.
(Continued)

*Primary Examiner* — William H. Beisner
(74) *Attorney, Agent, or Firm* — CANTOR COLBURN LLP

(57) ABSTRACT

The present disclosure provides advantageous rotary interfaces for fluid assemblies (e.g., rotary interfaces for fluid flow in bioreactor applications), and related methods of fabrication and use. More particularly, the present disclosure provides improved rotary interfaces for fluid flow through porous impellers for filtration and/or sparging for fluid assemblies (e.g., bioreactor applications), and related methods of fabrication and use. Disclosed herein is a fluid assembly (e.g., bioreactor) that includes a porous impeller which is in fluid communication with a hollow shaft that can be used to transport a reaction fluid to an external storage tank or the like. The fluid assembly/bioreactor can include a coupling mechanism that transmits rotary motion from a motor to a primary shaft and then to a hollow secondary shaft, while at the same time permitting removal of a filtrate
(Continued)

from the fluid assembly or bioreactor via the hollow secondary shaft and a porous impeller.

47 Claims, 17 Drawing Sheets

(51) Int. Cl.

| | |
|---|---|
| ***B01D 33/74*** | (2006.01) |
| ***B01D 33/80*** | (2006.01) |
| ***B01D 39/20*** | (2006.01) |
| ***B01F 27/053*** | (2022.01) |
| ***B01F 27/07*** | (2022.01) |
| ***B01F 27/072*** | (2022.01) |
| ***B01F 27/1131*** | (2022.01) |
| ***B01F 27/191*** | (2022.01) |
| ***B01F 27/2121*** | (2022.01) |
| ***B01F 27/2122*** | (2022.01) |
| ***B01F 27/2123*** | (2022.01) |
| ***B01F 27/91*** | (2022.01) |
| ***B05D 1/18*** | (2006.01) |
| ***C12M 1/00*** | (2006.01) |
| ***C12M 1/04*** | (2006.01) |

(52) U.S. Cl.

CPC ....... *B01D 33/801* (2013.01); *B01D 39/2027* (2013.01); *B01F 27/0531* (2022.01); *B01F 27/0722* (2022.01); *B01F 27/0723* (2022.01); *B01F 27/074* (2022.01); *B01F 27/1131* (2022.01); *B01F 27/191* (2022.01); *B01F 27/2121* (2022.01); *B01F 27/2122* (2022.01); *B01F 27/2123* (2022.01); *B01F 27/91* (2022.01); *B05D 1/18* (2013.01); *C12M 23/20* (2013.01); *C12M 27/04* (2013.01); *C12M 29/04* (2013.01); *C12M 29/06* (2013.01); *B01D 2201/34* (2013.01); *B01D 2239/0407* (2013.01); *B01D 2239/0478* (2013.01); *B01D 2239/10* (2013.01); *B01D 2239/1216* (2013.01); *B01D 2239/1241* (2013.01); *B01D 2239/1291* (2013.01)

(56) References Cited

U.S. PATENT DOCUMENTS

| | | | | |
|---|---|---|---|---|
| 3,997,447 | A * | 12/1976 | Breton | B01D 33/27 210/791 |
| 4,120,911 | A | 10/1978 | Davidson | |
| 4,290,885 | A * | 9/1981 | Kwak | C02F 3/207 210/197 |
| 4,535,062 | A | 8/1985 | Muller | |
| 4,717,485 | A | 1/1988 | Brunsell et al. | |
| 4,925,557 | A | 5/1990 | Ahlberg, Jr. et al. | |
| 4,936,986 | A | 6/1990 | Tarves, Jr. | |
| 5,057,284 | A | 10/1991 | Emmet, Jr. et al. | |
| 5,318,360 | A | 6/1994 | Langer et al. | |
| 5,364,450 | A * | 11/1994 | Eckert | B01F 33/451 75/681 |
| 5,904,894 | A | 5/1999 | Mukohda | |
| 6,146,443 | A | 11/2000 | Eckert | |
| 6,270,061 | B1 | 8/2001 | Bouquet et al. | |
| 8,506,198 | B2 | 8/2013 | West et al. | |
| 9,656,217 | B2 | 5/2017 | Jeong | |
| 10,214,715 | B2 | 2/2019 | Navran, Jr. | |
| 10,632,433 | B2 | 4/2020 | Claes et al. | |
| 2003/0116496 | A1 | 6/2003 | Schepis | |
| 2008/0257819 | A1 | 10/2008 | Tarves | |
| 2010/0258509 | A1* | 10/2010 | Iwaki | B01F 27/1151 261/87 |
| 2019/0083947 | A1 | 3/2019 | Goodwin et al. | |
| 2020/0318054 | A1 | 10/2020 | Cuello et al. | |

FOREIGN PATENT DOCUMENTS

| | | | |
|---|---|---|---|
| CN | 204656377 | U | 9/2015 |
| CN | 205392401 | U | 7/2016 |
| CN | 106552539 | A | 4/2017 |
| CN | 109364779 | A | 2/2019 |
| CN | 112546734 | A | 3/2021 |
| GB | 617677 | A | 2/1949 |

OTHER PUBLICATIONS

Challener; "The Potential of Perfusion"; Pharm. Techn., vol. 39, Issue 8; 2015; pp. 36-38.

Clincke et al.; "Very High Density of CHO Cells in Perfusion by ATF or TFF in WAVE Bioreactor™ Part I. Effect of the Cell Density on the Process," Biotechnol. Prog., vol. 29, No. 3; 2013; pp. 754-767.

Femmer et al.; "A Membrane Stirrer for Product Recovery and Substrate Feeding"; Biotechnology and Bioengineering, vol. 112, No. 2; 2015; pp. 331-338.

Fisher et al.; "The Current Scientific and Regulatory Landscape in Advancing Integrated Continuous Biopharmaceutical Manufacturing"; Trends in Biotech., vol. 37, Issue 3; 2019; pp. 253-267.

Hernandez; "Continuous Manufacturing: A Changing Processing Paradigm"; BioPharm International, vol. 28, No. 4; 2015; 8 pages.

Lehr et al.; "Perfusion in the 21st Century"; BioPharm International, vol. 29, Issue 8; 2016; pp. 24-26.

Pinto et al.; "Wide-surface pore microfiltration membrane drastically improves sieving decay in TFF-based perfusion cell culture and streamline chromatography integration for continuous bioprocessing"; Biotechnology & Bioengineering, vol. 117; 2020; pp. 3336-3344.

Rader et al.; "Economics of Perfusion Culture Media and Upstream Processing"; American Pharmaceutical Review; 2021; 7 pages.

Tapia et al.; "Bioreactors for high cell density and continuous multi-stage cultivations: options for process intensification in cell culture-based viral vaccine production"; Appl Microbiol Biotechnol, vol. 100; 2016; pp. 2121-2132.

U.S. Food and Drug Administration; "Pharmaceutical CGMPs for the 21st Century—A Risk-Based Approach Final Report"; 2004; 32 pages.

Zhao et al.; "Design of Lubricant-Infused Surfaces Based on Mussel-Inspired Nanosilica Coatings: Solving Adhesion by Pre-Adhesion"; Langmuir, vol. 37, No. 36; 2021; pp. 10708-10719.

International Search Report for International Application No. PCT/US2022/032769; International Filing Date Jun. 9, 2022; Date of Mailing Nov. 7, 2022; 6 pages.

Written Opinion for International Application No. PCT/US2022/032769; International Filing Date Jun. 9, 2022; Date of Mailing Nov. 7, 2022; 17 pages.

Supplementary European Search Report for the corresponding European Application No. 22821003, Date of Mailing: Apr. 2, 2025; 8 pages.

* cited by examiner

ROTARY INTERFACE FOR FLUID ASSEMBLIES AND RELATED METHODS OF FABRICATION AND USE

CROSS-REFERENCE TO RELATED APPLICATION

The present application claims priority benefit to a provisional application which was filed on Jun. 9, 2021, and assigned Ser. No. 63/208,897. The entire contents of the foregoing provisional application is incorporated herein by reference.

FIELD OF THE DISCLOSURE

The present disclosure relates to rotary interfaces for fluid assemblies (e.g., rotary interfaces for fluid flow in bioreactor applications) and related methods of fabrication and use and, more particularly, to rotary interfaces for fluid flow through porous impellers for filtration and/or sparging for fluid assemblies (e.g., bioreactor applications) and related methods of fabrication and use.

BACKGROUND OF THE DISCLOSURE

In general, some fluid assemblies (e.g., bioreactor assemblies) used for processes such as fermentation or the like are typically conducted in reactors that include solid impellers and shafts. In order to separate the components included in the reactor, the reactor has to be drained and the products obtained therefrom subjected to a second process that involves filtration, centrifugation, and the like. In addition, the solid impeller and the shaft have to be removed from the reactor to be cleaned (in a separate cleaning process) before other products can be produced in the reactor.

An interest exists for improved fluid assemblies and related methods of fabrication and use.

These and other inefficiencies and opportunities for improvement are addressed and/or overcome by the assemblies, systems and methods of the present disclosure.

BRIEF SUMMARY OF THE DISCLOSURE

The present disclosure provides advantageous rotary interfaces for fluid assemblies (e.g., rotary interfaces for fluid flow in bioreactor applications), and related methods of fabrication and use. More particularly, the present disclosure provides improved rotary interfaces for fluid flow through porous impellers for filtration and/or sparging for fluid assemblies (e.g., bioreactor applications), and related methods of fabrication and use.

The present disclosure provides for a fluid assembly including a vessel configured to house a fluid; a motor in operative communication with a shaft, and a first porous impeller mounted with respect to the shaft, the first porous impeller configured to be immersed in the fluid housed in the vessel so that when rotary motion from the motor is transferred to the first porous impeller, the first porous impeller moves and agitates the fluid; wherein filtrate from the fluid can be extracted from the vessel via the first porous impeller.

The present disclosure also provides for a fluid assembly wherein the vessel is a bioreactor. The present disclosure also provides for a fluid assembly wherein the filtrate can be extracted from the vessel without changing speed or position of the first porous impeller.

The present disclosure also provides for a fluid assembly wherein the first porous impeller is a first micro-porous impeller; and wherein the first micro-porous impeller has pores having a range of pores sizes of from about 50 nanometers to about 60 micrometers.

The present disclosure also provides for a fluid assembly wherein the first porous impeller is in fluid communication with a hollow portion of the shaft, and the filtrate can be extracted from the vessel via the hollow portion of the shaft; and wherein the hollow portion of the shaft discharges the filtrate to a discharge conduit.

The present disclosure also provides for a fluid assembly wherein the shaft includes a primary shaft and a hollow secondary shaft; and wherein the filtrate can be extracted from the vessel without detaching the primary shaft from the hollow secondary shaft.

The present disclosure also provides for a fluid assembly wherein the primary shaft is laterally offset from the hollow secondary shaft. The present disclosure also provides for a fluid assembly wherein an axis of the primary shaft is concentric with an axis of the hollow secondary shaft. The present disclosure also provides for a fluid assembly wherein the primary shaft can detachably communicate with the hollow secondary shaft.

The present disclosure also provides for a fluid assembly wherein the primary shaft is in operative communication with the hollow secondary shaft via an idling shaft; and wherein the primary shaft, the hollow secondary shaft and the idling shaft are in rotary communication with each other via gears or a belt drive.

The present disclosure also provides for a fluid assembly wherein the motor can be moved laterally to engage the primary shaft with the hollow secondary shaft. The present disclosure also provides for a fluid assembly wherein the hollow secondary shaft is in fluid communication with the porous impeller and discharges fluid to a discharge conduit.

The present disclosure also provides for a fluid assembly wherein the discharge conduit contacts the hollow secondary shaft via a bearing which permits the hollow secondary shaft to rotate while permitting the discharge conduit to remain stationary.

The present disclosure also provides for a fluid assembly wherein the discharge conduit contacts the hollow secondary shaft via a seal which prevents fluid leakage. The present disclosure also provides for a fluid assembly wherein the hollow secondary shaft comprises an outlet port for filtrate removal from the vessel, the outlet port in fluid communication with a discharge conduit. The present disclosure also provides for a fluid assembly wherein the shaft includes a hollow primary shaft and a hollow secondary shaft. The present disclosure also provides for a fluid assembly wherein the hollow primary shaft comprises an outlet port for filtrate removal from the vessel, the outlet port in fluid communication with a discharge conduit.

The present disclosure also provides for a fluid assembly wherein an axis of the hollow primary shaft is concentric with an axis of the hollow secondary shaft. The present disclosure also provides for a fluid assembly wherein the hollow secondary shaft is in fluid communication with the first porous impeller and discharges filtrate to a discharge conduit that contacts the hollow primary shaft. The present disclosure also provides for a fluid assembly wherein the discharge conduit contacts the hollow primary shaft via a bearing which permits the hollow primary shaft to rotate while permitting the discharge conduit to remain stationary. The present disclosure also provides for a fluid assembly wherein the discharge conduit contacts the hollow primary shaft via a seal which prevents fluid leakage.

The present disclosure also provides for a fluid assembly further including a central hollow region for supporting the hollow secondary shaft, the central hollow region comprising: (i) a plurality of adapter plates with o-ring seals for non-rotating surfaces and lip seals for the rotating hollow secondary shaft to seal to the adapter plates; (ii) a central region situated between the adapter plates that is in operative communication with an exit port in the hollow secondary shaft, the central region being operative to receive the filtrate and to discharge the filtrate to the discharge conduit; and (iii) at least one connector disposed on at least one side of one of the adapter plates to attach to the vessel.

The present disclosure also provides for a fluid assembly wherein the first porous impeller includes an outer surface, the outer surface substantially porous throughout the outer surface of the first porous impeller. The present disclosure also provides for a fluid assembly wherein the first porous impeller includes an outer surface, the outer surface porous at pre-determined locations of the outer surface of the first porous impeller.

The present disclosure also provides for a fluid assembly wherein the first porous impeller is fabricated from at least one of metals, polymers or ceramics.

The present disclosure also provides for a fluid assembly further including a second impeller mounted with respect to the shaft, and wherein the second impeller is porous or non-porous.

The present disclosure also provides for a fluid assembly further including at least one porous sparging member mounted with respect to the shaft; and wherein at least a portion of the shaft provides a fluid path for fluid or gas through the at least one porous sparging member; and wherein the at least one porous sparging member is a porous tube, plate, ring or tree.

The present disclosure also provides for a fluid assembly wherein the first porous impeller or the at least one porous sparging member is fabricated by disposing a porous metal substrate in a coating solution that comprises metallic or nonmetallic coating particles; subjecting the porous metal substrate to a positive pressure to drive the coating solution through the porous metal substrate; or alternatively subjecting the porous metal substrate to a negative pressure to drive the coating solution through the porous metal substrate; or alternatively disposing the metallic or nonmetallic coating particles on a surface of the porous metal substrate via a process of dipping the porous metal substrate into the coating solution while removing the solvent at a controlled rate to deposit a coating layer on the porous metal substrate to form the first porous impeller or the at least one porous sparging member.

The present disclosure also provides for a fluid assembly wherein the first porous impeller comprises a first blade and a second blade. The present disclosure also provides for a fluid assembly wherein the first and second blades of the first porous impeller are angled relative to a horizontal plane of a bottom surface of the shaft. The present disclosure also provides for a fluid assembly wherein the first and second blades of the first porous impeller are angled from about 30° to about 60° relative to a horizontal plane of a bottom surface of the shaft.

The present disclosure also provides for a fluid assembly further including a second porous impeller mounted with respect to the shaft, the second porous impeller comprising a first blade and a second blade; and wherein filtrate from the fluid can be extracted from the vessel via the second porous impeller. The present disclosure also provides for a fluid assembly wherein the first and second blades of the second porous impeller are angled relative to the horizontal plane of the bottom surface of the shaft.

The present disclosure also provides for a fluid assembly wherein the first and second blades of the second porous impeller are angled at a different and lower angle relative to the horizontal plane of the bottom surface of the shaft than the angle of the first and second blades of the first porous impeller. The present disclosure also provides for a fluid assembly wherein the first and second blades of the second porous impeller are co-planar relative to the horizontal plane of the bottom surface of the shaft. The present disclosure also provides for a fluid assembly wherein the first porous impeller comprises a single contiguous body.

The present disclosure also provides for a fluid assembly wherein the first porous impeller is a disk or a wheel. The present disclosure also provides for a fluid assembly wherein a porous region of the first porous impeller is spaced a distance from the shaft.

The present disclosure also provides for a fluid assembly further including a second impeller mounted with respect to the shaft, the second impeller comprising a first blade and a second blade, the first and second blades of the second porous impeller angled relative to the horizontal plane of the bottom surface of the shaft. The present disclosure also provides for a fluid assembly wherein the first porous impeller is co-planar relative to the horizontal plane of the bottom surface of the shaft.

The present disclosure also provides for a fluid assembly further including a head plate at a top portion of the vessel; and wherein at least a portion of the discharge conduit is positioned below the head plate. The present disclosure also provides for a fluid assembly further including a head plate at a top portion of the vessel; and wherein the seal is positioned below the head plate.

The present disclosure also provides for a fluid assembly further including a housing surrounding at least a portion of the first porous impeller, the housing configured to create pressure on the first porous impeller to promote fluid flow through the first porous impeller. The present disclosure also provides for a fluid assembly wherein the housing is an inverted cup housing; and wherein a top surface of the housing has at least one opening.

The present disclosure also provides for a fluid assembly wherein the shaft includes an upper manifold and a lower manifold, the upper manifold mounted with respect to the lower manifold by a first side member and a second side member, and the first porous impeller mounted with respect to the first and second side members. The present disclosure also provides for a fluid assembly further including a second porous impeller mounted with respect to the first and second side members. The present disclosure also provides for a fluid assembly wherein the second porous impeller is configured to be positioned at a different elevational position than the first porous impeller within the vessel. The present disclosure also provides for a fluid assembly wherein the first and second side members comprise flexible ropes.

The present disclosure also provides for a fluid assembly wherein a first exterior edge of the first porous impeller is connected to the first side member, and a second exterior edge of the first porous impeller is connected to the second side member. The present disclosure also provides for a fluid assembly wherein filtrate from the fluid can be extracted from the vessel via the first porous impeller, the first and second side members and the lower manifold. The present disclosure also provides for a fluid assembly wherein the lower manifold is mounted with respect to a rotary fluid port.

The present disclosure also provides for a fluid assembly including a vessel configured to house a fluid; a motor in operative communication with a shaft, and a first impeller mounted with respect to the shaft, the first impeller configured to be immersed in the fluid housed in the vessel so that when rotary motion from the motor is transferred to the first impeller, the first impeller moves and agitates the fluid; a porous housing surrounding at least a portion of the first impeller; wherein filtrate from the fluid can be extracted from the vessel via the porous housing; and wherein the first impeller is porous or non-porous.

The present disclosure also provides for a fluid assembly wherein the porous housing is an inverted cup housing; and wherein a top surface of the porous housing has at least one opening.

The present disclosure also provides for a fluid assembly wherein the porous housing includes an internal surface that is porous and an exterior surface that is non-porous, and an internal void volume that separates an outer diameter of the housing from an inner diameter of the housing; and wherein a fluid flow tube connects to the internal void volume and allows filtrate to be extracted from the vessel.

The present disclosure provides for a filtration method including charging a fluid to a vessel; providing a motor in operative communication with a shaft; mounting a first porous impeller with respect to the shaft; immersing the first porous impeller in the fluid housed in the vessel; wherein when rotary motion from the motor is transferred to the first porous impeller, the first porous impeller moves and agitates the fluid; and filtering the fluid with the porous impeller to create a filtrate; and extracting the filtrate from the fluid via the first porous impeller.

The present disclosure also provides for a filtration method wherein the vessel is a bioreactor; wherein the filtrate can be extracted from the vessel without changing speed or position of the first porous impeller; wherein the first porous impeller is a first micro-porous impeller that has pores having a range of pores sizes of from about 50 nanometers to about 60 micrometers; wherein the first porous impeller is in fluid communication with a hollow portion of the shaft, and the filtrate can be extracted from the vessel via the hollow portion of the shaft; and wherein the hollow portion of the shaft discharges the filtrate to a discharge conduit.

The present disclosure also provides for a filtration method wherein the shaft includes a primary shaft and a hollow secondary shaft; and wherein the filtrate can be extracted from the vessel without detaching the primary shaft from the hollow secondary shaft. The present disclosure also provides for a filtration method wherein an axis of the primary shaft is concentric with an axis of the secondary hollow shaft. The present disclosure also provides for a filtration method wherein the primary shaft is laterally offset from the hollow secondary shaft.

The present disclosure provides for a coating method including disposing a porous metal substrate in a coating solution that comprises metallic or nonmetallic coating particles; subjecting the porous metal substrate to a positive pressure to drive the coating solution through the porous metal substrate; or alternatively subjecting the porous metal substrate to a negative pressure to drive the coating solution through the porous metal substrate; or alternatively disposing the metallic or nonmetallic coating particles on a surface of the porous metal substrate via a process of dipping the porous metal substrate into the coating solution while removing the solvent at a controlled rate to deposit a coating layer on the porous metal substrate to form a coated porous metal member.

The present disclosure also provides for a coating method wherein the coated porous metal member is a porous impeller or a porous sparging member. The present disclosure also provides for a coating method wherein the porous metal substrate is subjected to sintering to diffusion bond the coating particles to the porous metal substrate. The present disclosure also provides for a coating method wherein the porous metal substrate comprises stainless steel.

The present disclosure also provides for a coating method wherein the porous metal substrate has the same composition or a different composition as the coating particles; and wherein the coating particles comprise at least one of stainless steel, titanium oxide or polyether ether ketone.

The present disclosure also provides for a coating method wherein the coating layer has a thickness of 20 to 200 micrometers; and wherein the metallic or nonmetallic coating particles have a mean particle size ranging from 50 nanometer to 100 micrometers. The present disclosure also provides for a coating method wherein the disposing of the porous metal substrate in the coating solution that comprises coating particles is conducted greater than or equal to two times. The present disclosure also provides for a coating method wherein the disposing of the porous metal substrate in the coating solution that comprises coating particles is conducted one to five times. The present disclosure also provides for a coating method wherein the porous metal substrate with the coating layer disposed thereon has an average pore size of 50 to 100 nanometers.

The present disclosure also provides for a coated article including a porous metal substrate having disposed thereon a coating layer comprising metallic or non-metallic coating particles; wherein the coating layer has a thickness of 20 to 200 micrometers; and wherein the porous metal substrate with the coating layer disposed thereon has an average pore size of 50 nanometers to 60 micrometers.

The present disclosure also provides for a coated article wherein the porous metal substrate comprises stainless steel. The present disclosure also provides for a coated article wherein the porous metal substrate has the same composition or a different composition as the coating particles. The present disclosure also provides for a coated article wherein the porous metal substrate with the coating layer disposed thereon has an average pore size of 500 nanometers to 60 micrometers.

The present disclosure also provides for a coated article wherein the coating particles comprise at least one of stainless steel, titanium oxide or polyether ether ketone. The present disclosure also provides for a coated article wherein the article is a porous impeller or a porous sparging member.

The above described and other features are exemplified by the following figures and detailed description.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

The following figures are exemplary embodiments wherein the like elements are numbered alike.

Features and aspects of embodiments are described below with reference to the accompanying drawings, in which elements are not necessarily depicted to scale.

Figure 1:
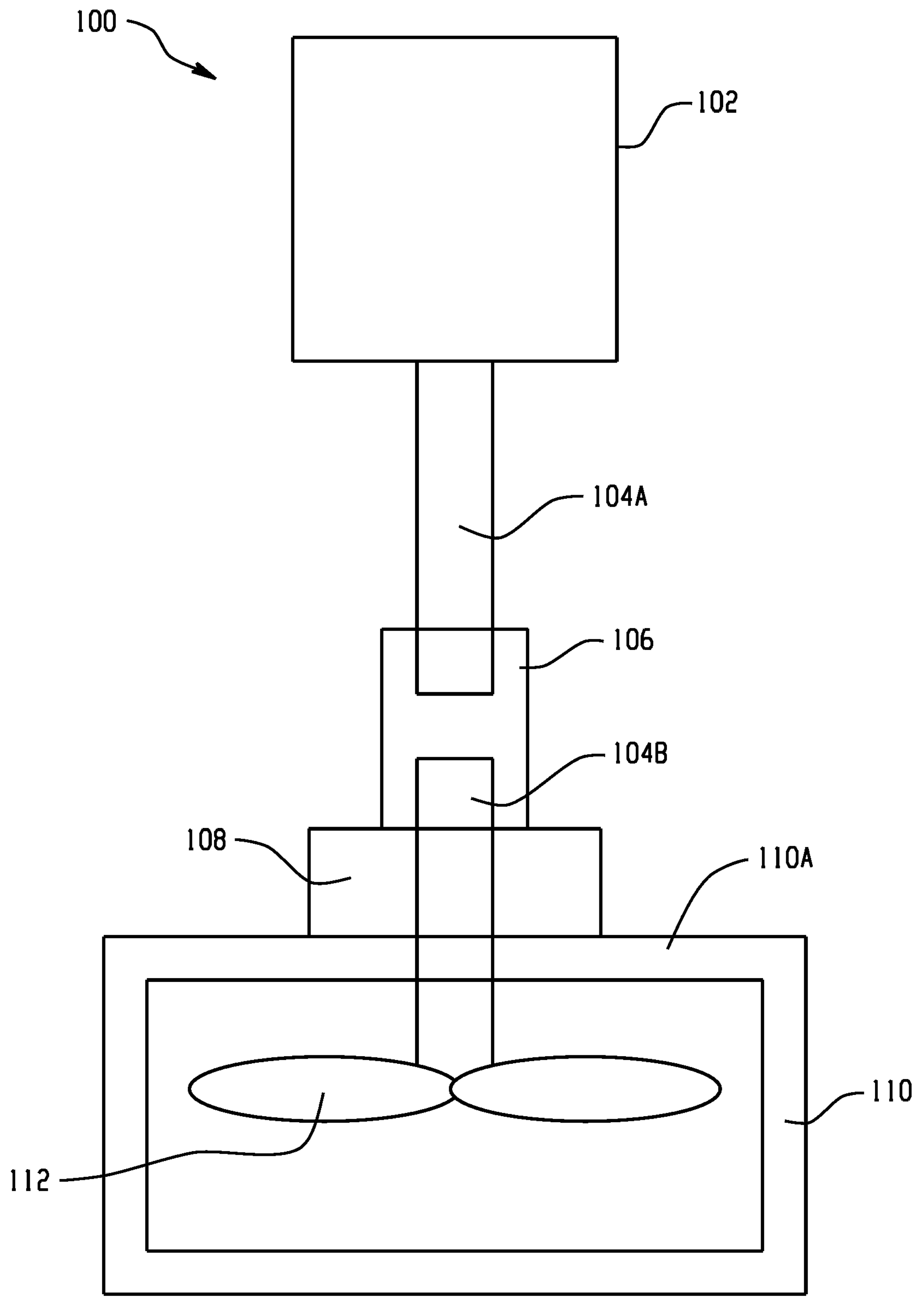

Exemplary embodiments of the present disclosure are further described with reference to the appended figures. It is to be noted that the various features, steps, and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein:

FIG. 1 is a schematic diagram of an example fluid assembly or bioreactor that includes a solid impeller and shaft.

Figure 2:
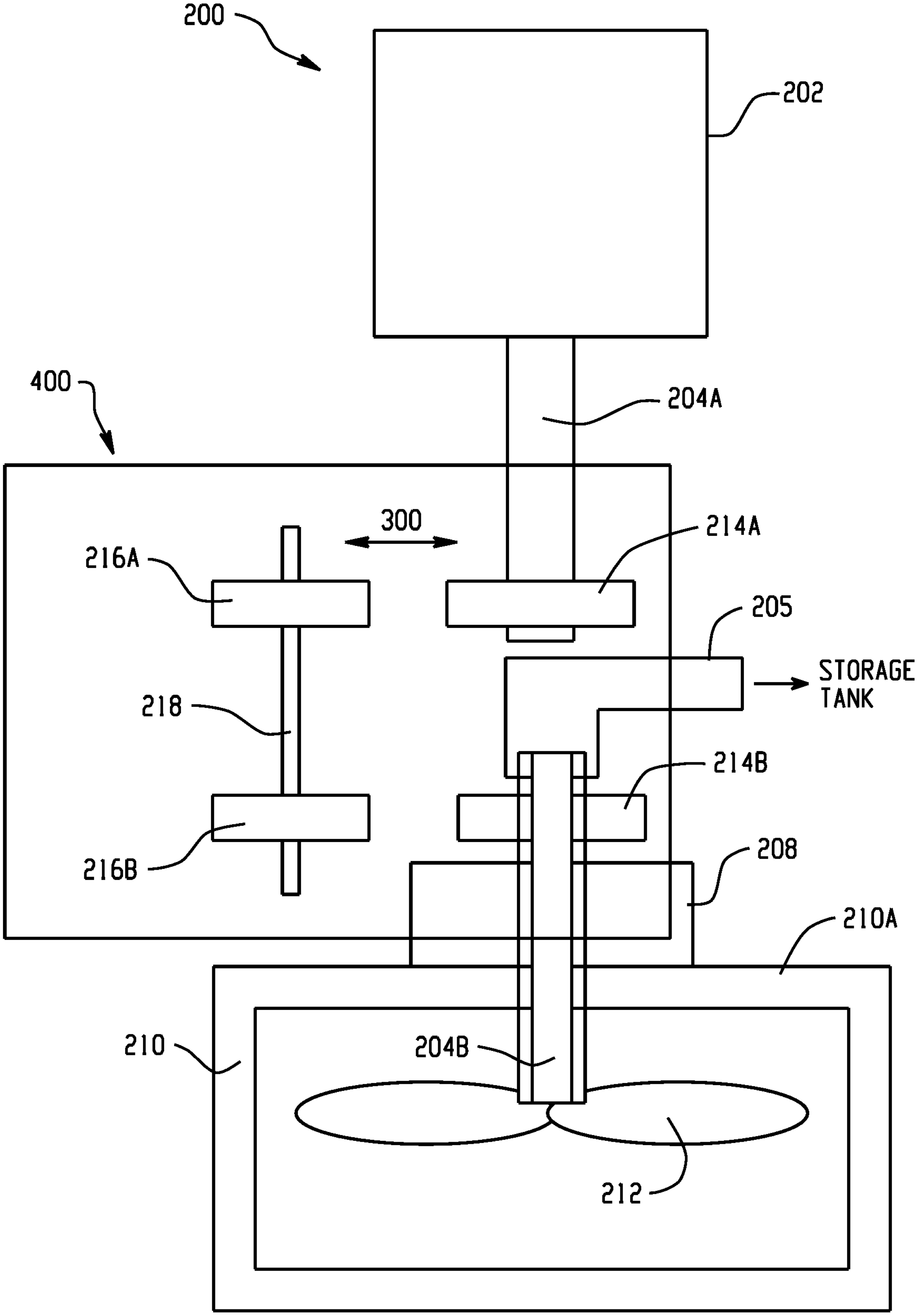

FIG. 2 depicts an exemplary embodiment of a fluid assembly where the primary shaft (the shaft in direct contact with the motor) is offset from the secondary shaft, according to the present disclosure.

Figure 3:
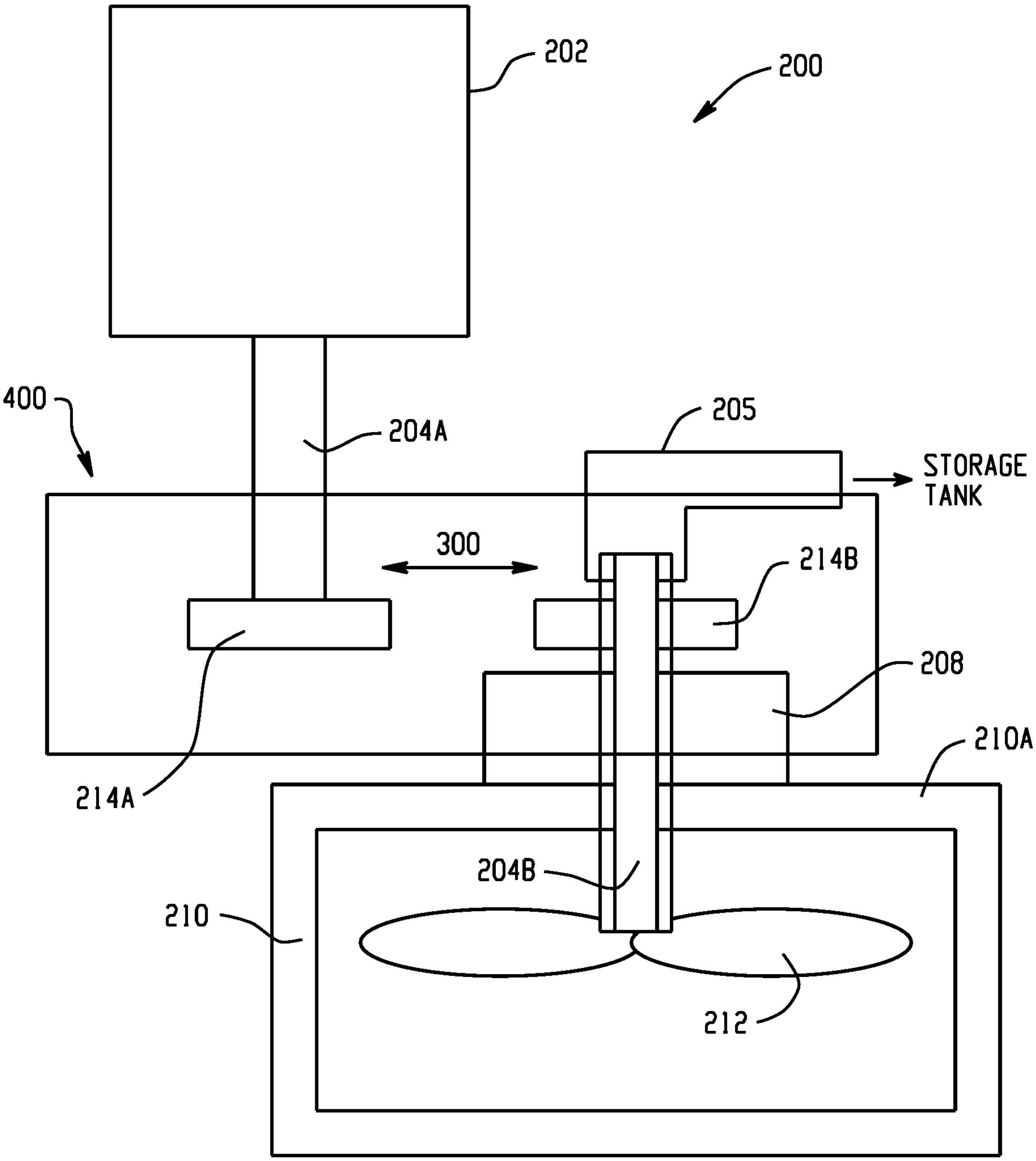

FIG. 3 depicts another exemplary embodiment of a fluid assembly where the primary shaft (the shaft in direct contact with the motor) is offset from the secondary shaft.

Figure 4:
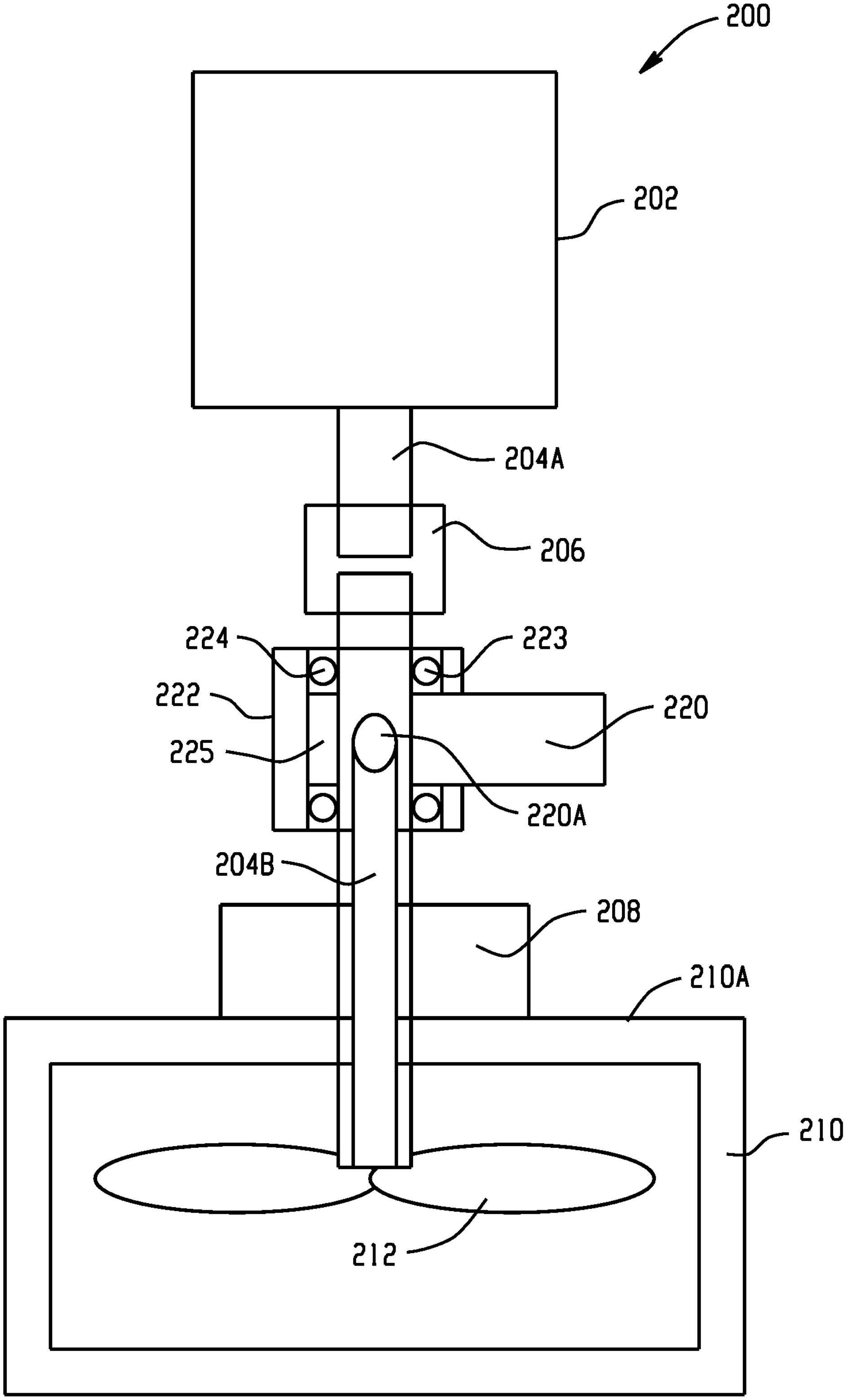

FIG. 4 depicts another exemplary embodiment of a fluid assembly where fluid is transported from the porous impeller to a discharge conduit that is in fluid communication with a port in the secondary shaft; the primary shaft is not offset from the secondary shaft.

Figure 5:
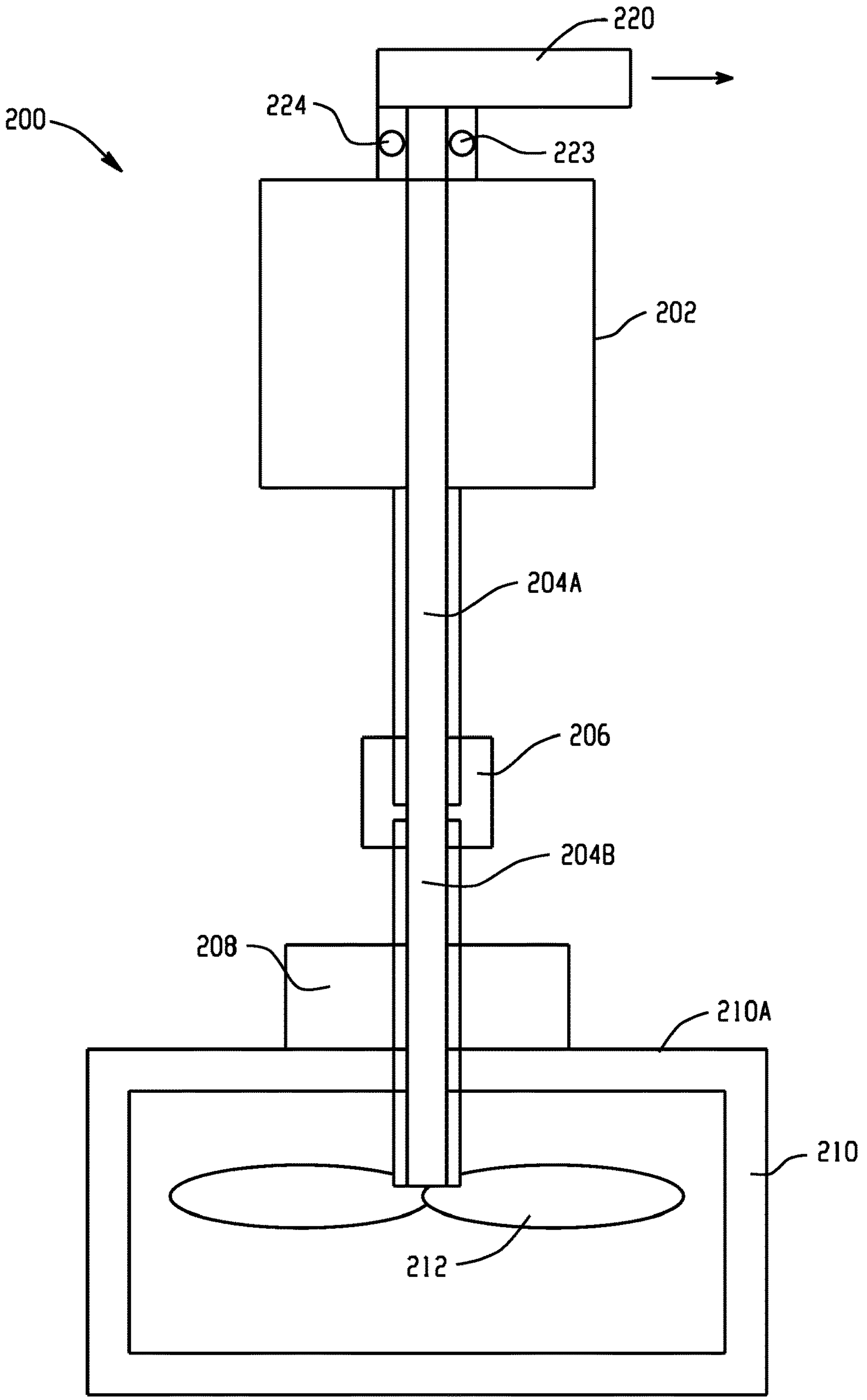

FIG. 5 is a schematic diagram of an example fluid assembly where fluid is transported from the porous impeller to a discharge conduit that is in fluid communication with a port in the primary shaft; the primary shaft is not offset from the secondary shaft.

Figure 6:
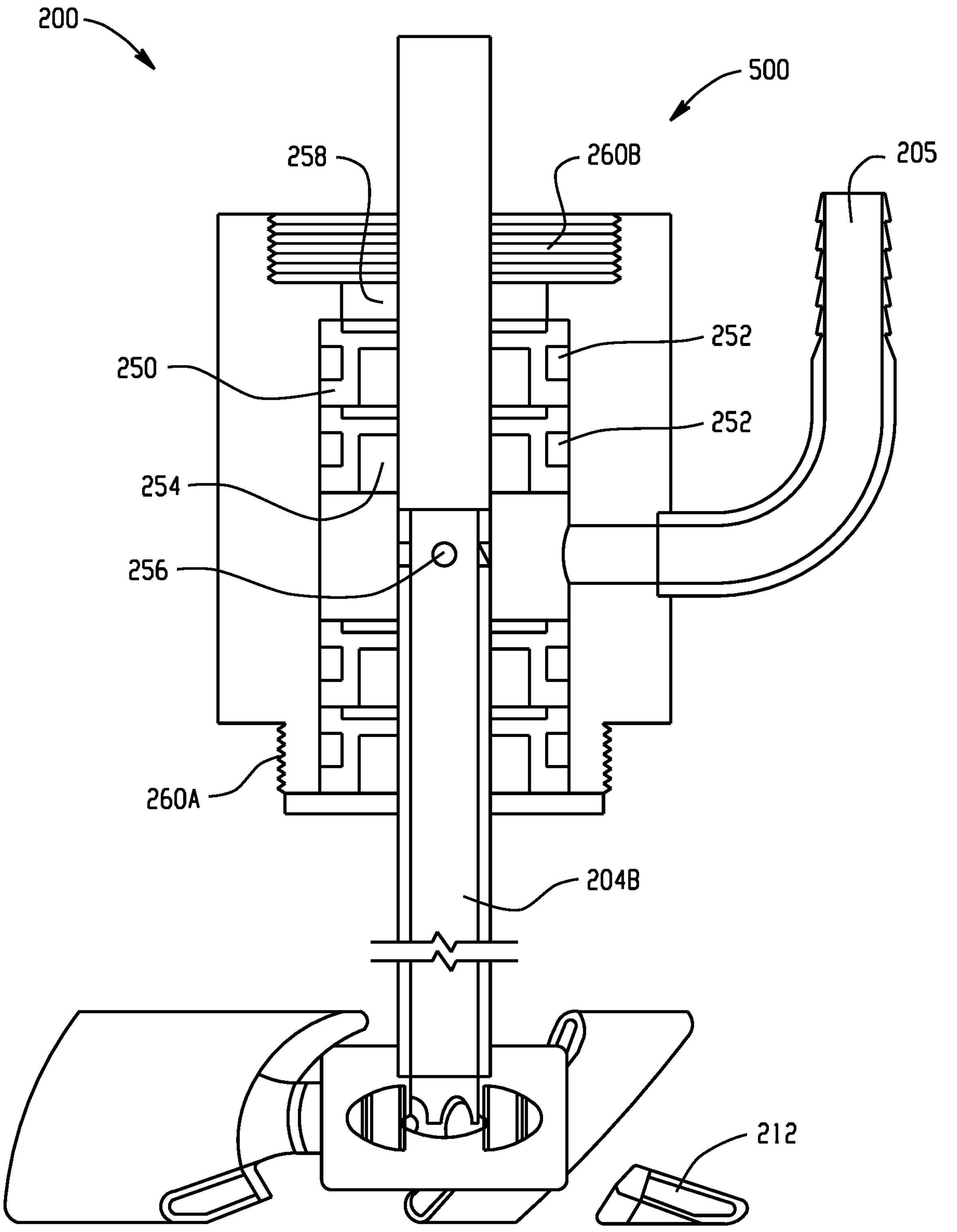

FIG. 6 is a depiction of another example coupling mechanism that facilitates coupling of the primary shaft with the secondary shaft.

Figure 7:
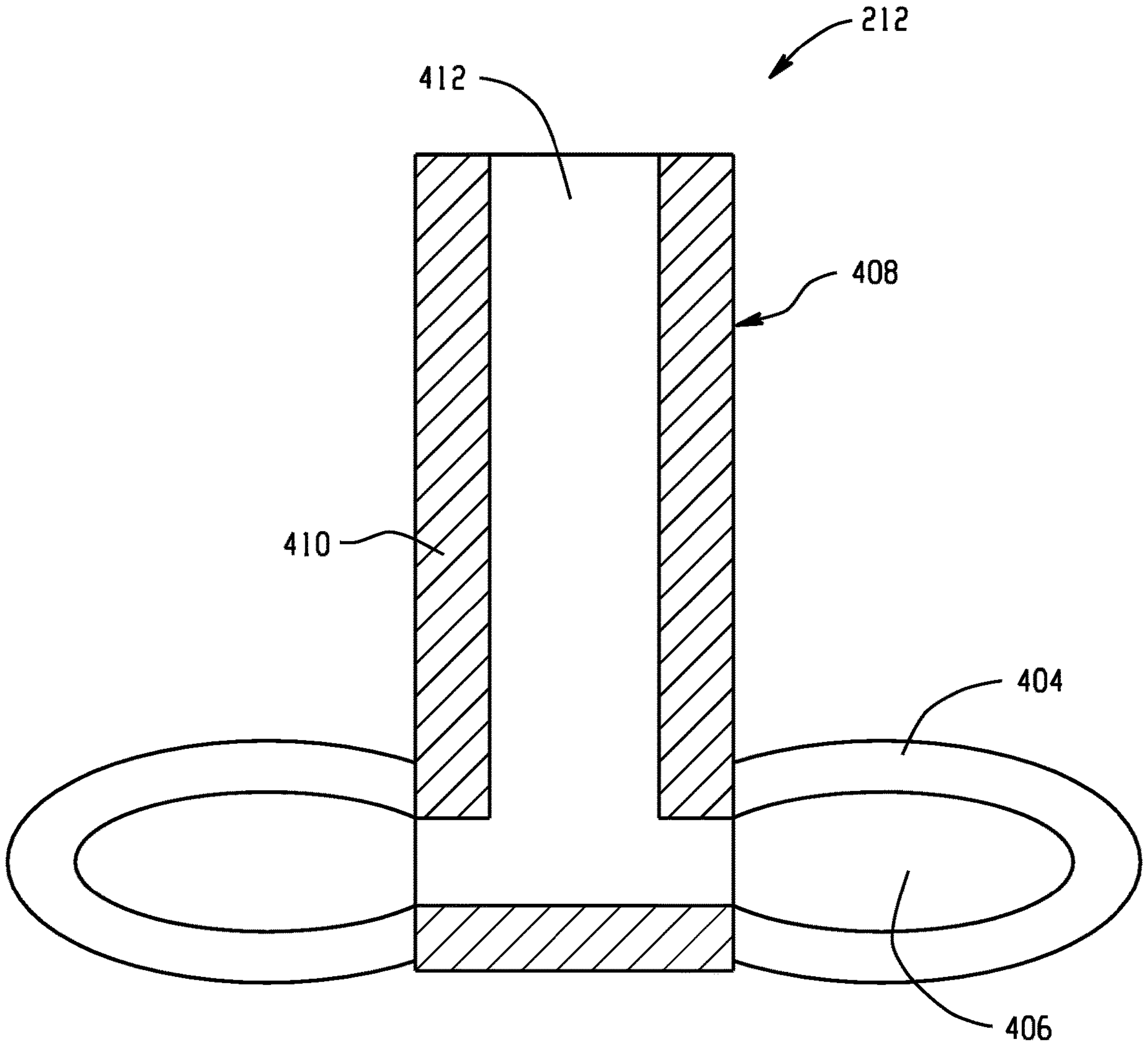

FIG. 7 depicts a cross-sectional view of another example coupling mechanism that is used to couple the primary shaft to the secondary shaft in FIGS. 4 and 5.

Figure 8:
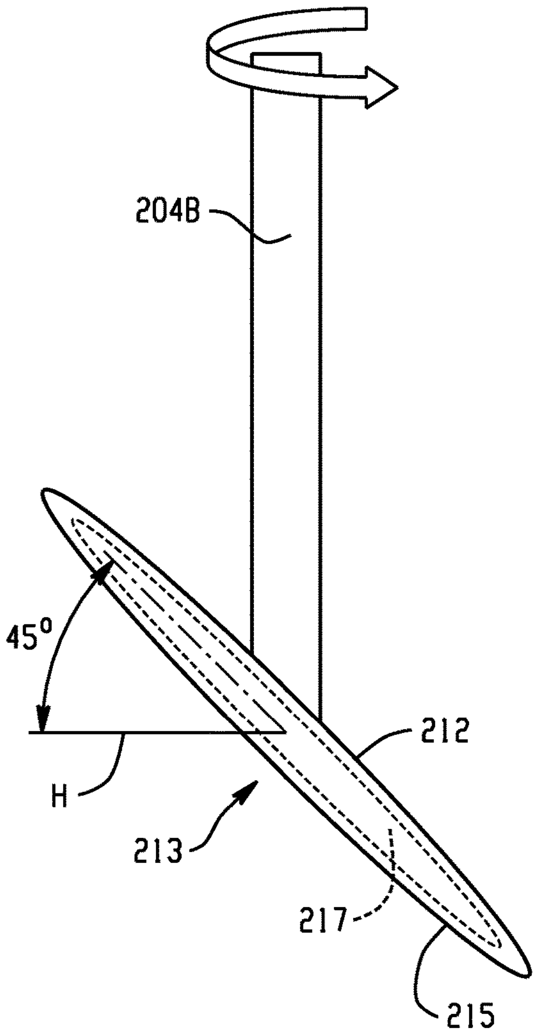

FIG. 8 is a side view schematic of an example hollow rotating shaft and impeller blade oriented at 45 degrees with respect to a horizontal surface; only a single blade is illustrated for the impeller.

Figure 9:
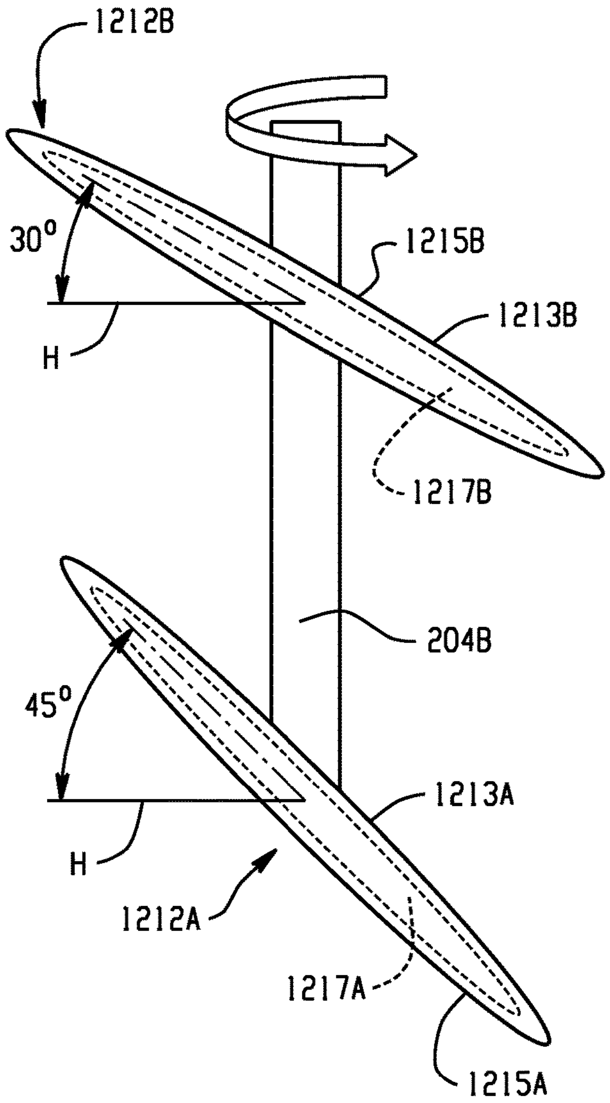

FIG. 9 is a side view schematic of an example hollow rotating shaft and two impellers with a first impeller with blades set at 45 degrees with respect to a horizontal surface, and a second impeller with blades set at 30 degrees with respect to a horizontal surface; only a single blade is illustrated for each impeller.

Figure 10:
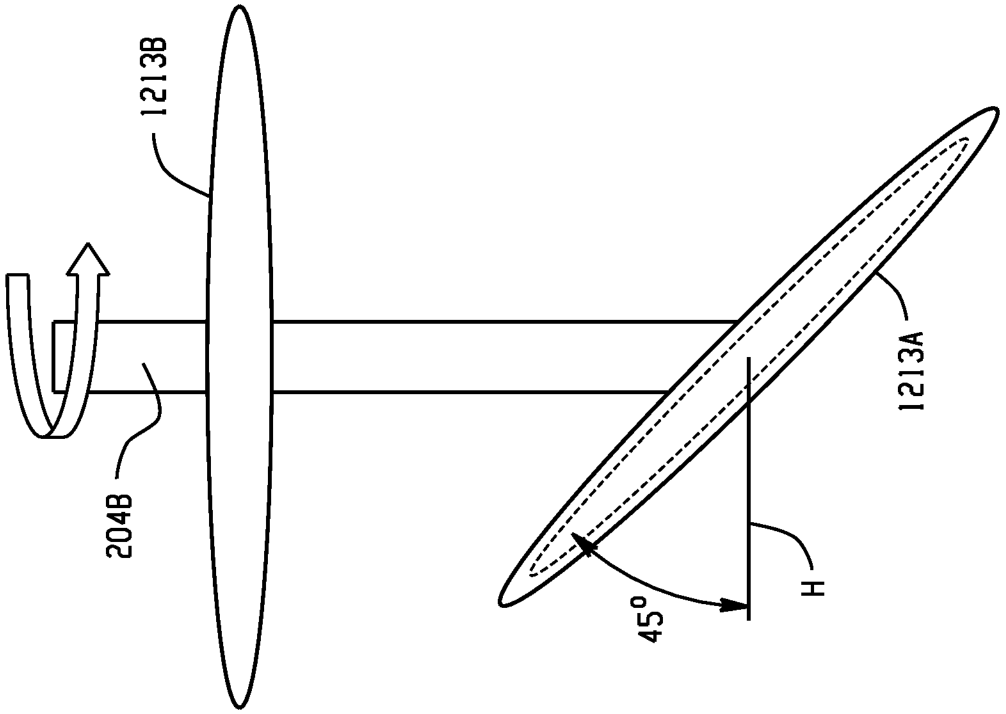

FIG. 10 is a side view schematic of a hollow rotating shaft and a first and second porous impeller, in which the blades of a first porous impeller are oriented at 45 degrees with respect to the horizontal, and the blades of a second porous impeller are oriented at 0 degrees with respect to the horizontal; only a single blade is illustrated for each impeller.

Figure 11:
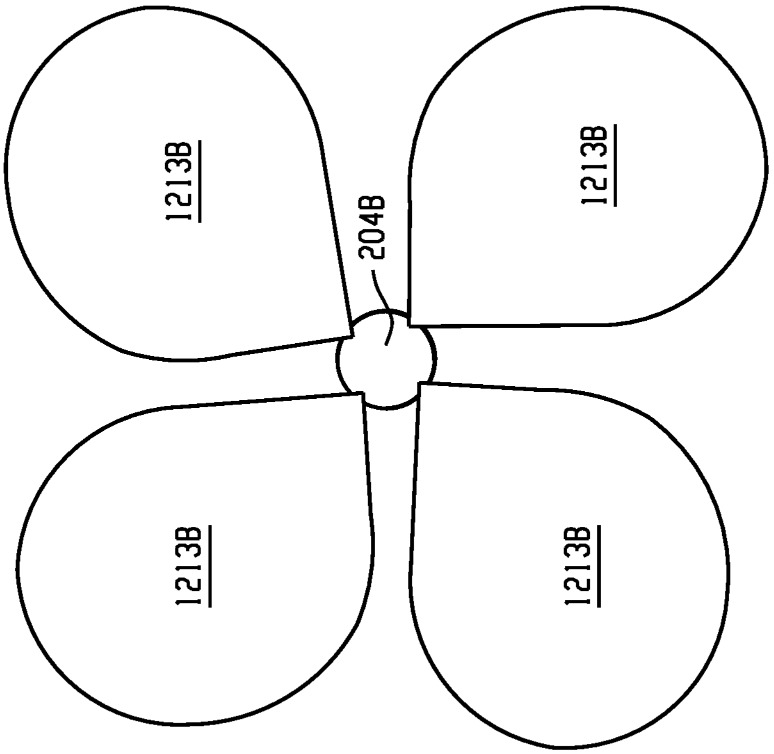

FIG. 11 is a top view of FIG. 10 showing, for example, four blades on the second impeller; the first impeller is omitted for clarity.

Figure 12:
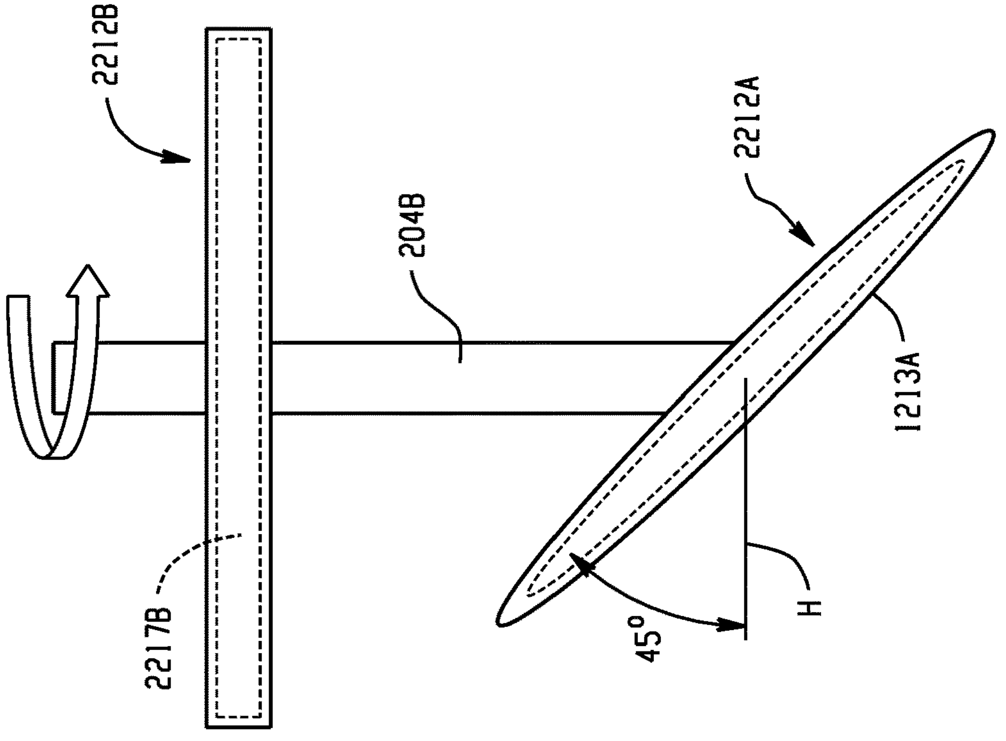

FIG. 12 is a side view schematic of a hollow rotating shaft connected to a first porous impeller, in which the blades of the first porous impeller are oriented at 45 degrees with respect to the horizontal, and a rotating porous disk connected to the hollow rotating shaft oriented substantially horizontally; only a single blade is illustrated for the first impeller.

Figure 13:
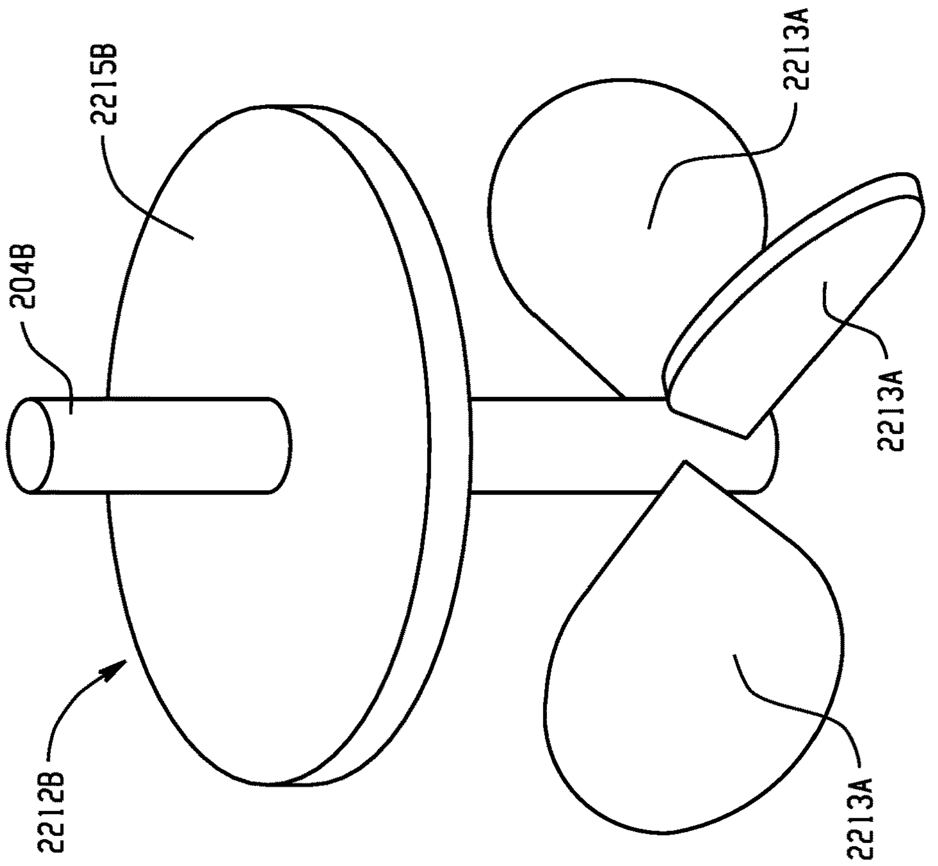

FIG. 13 is an iso side perspective view of FIG. 12.

Figure 14:
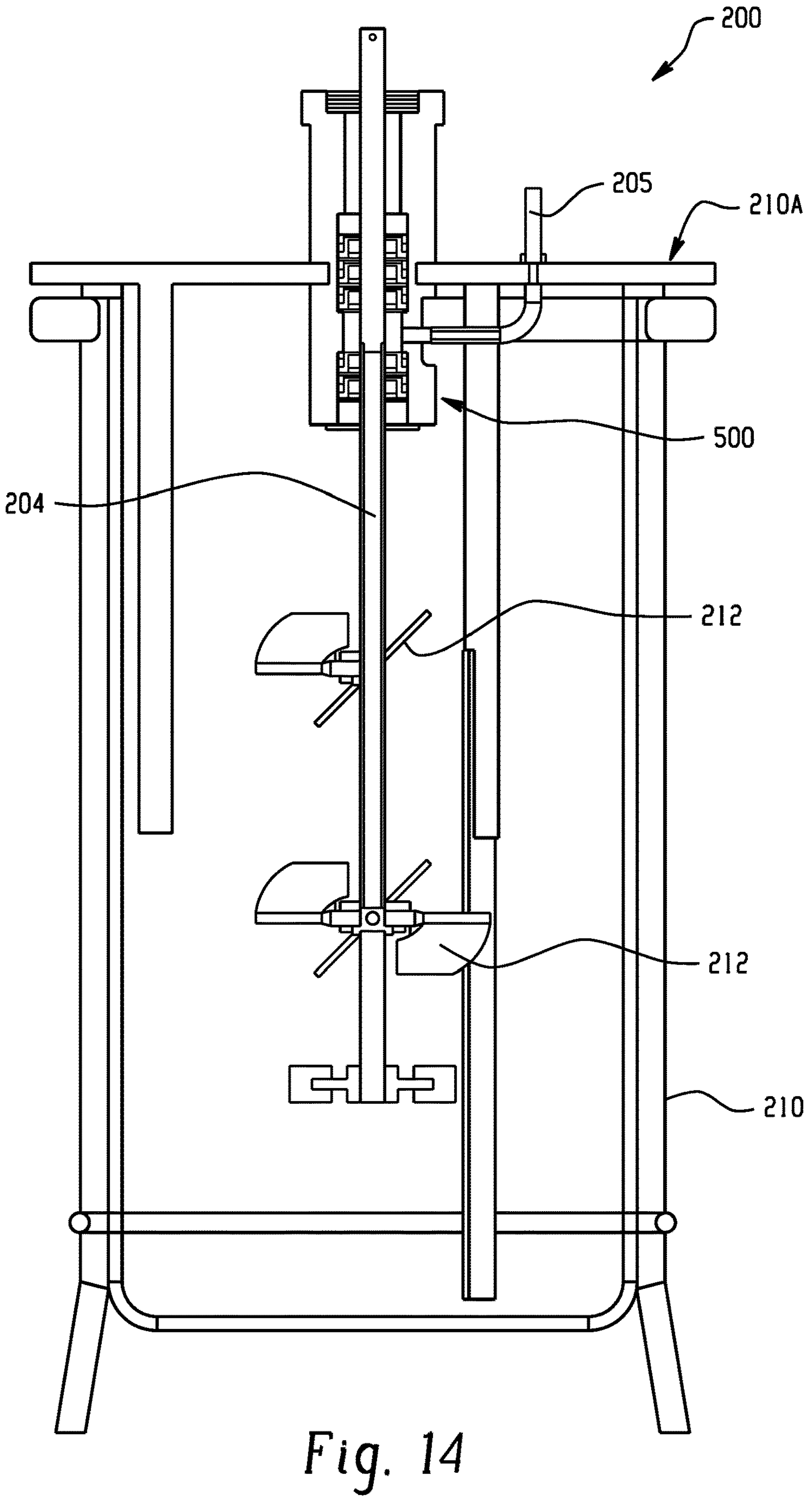

FIG. 14 is a side view of another exemplary fluid assembly.

Figure 15:
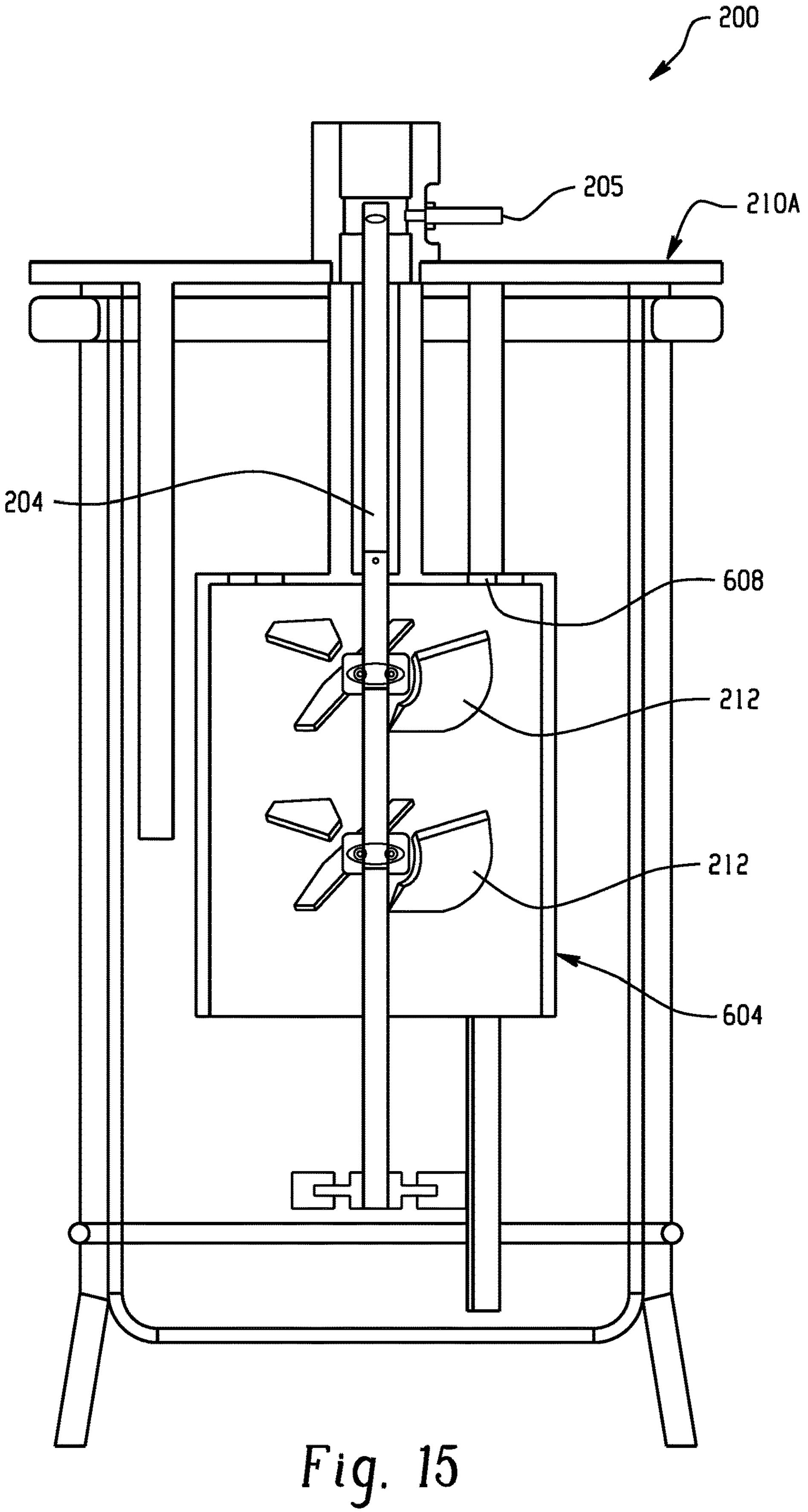
Figure 16:
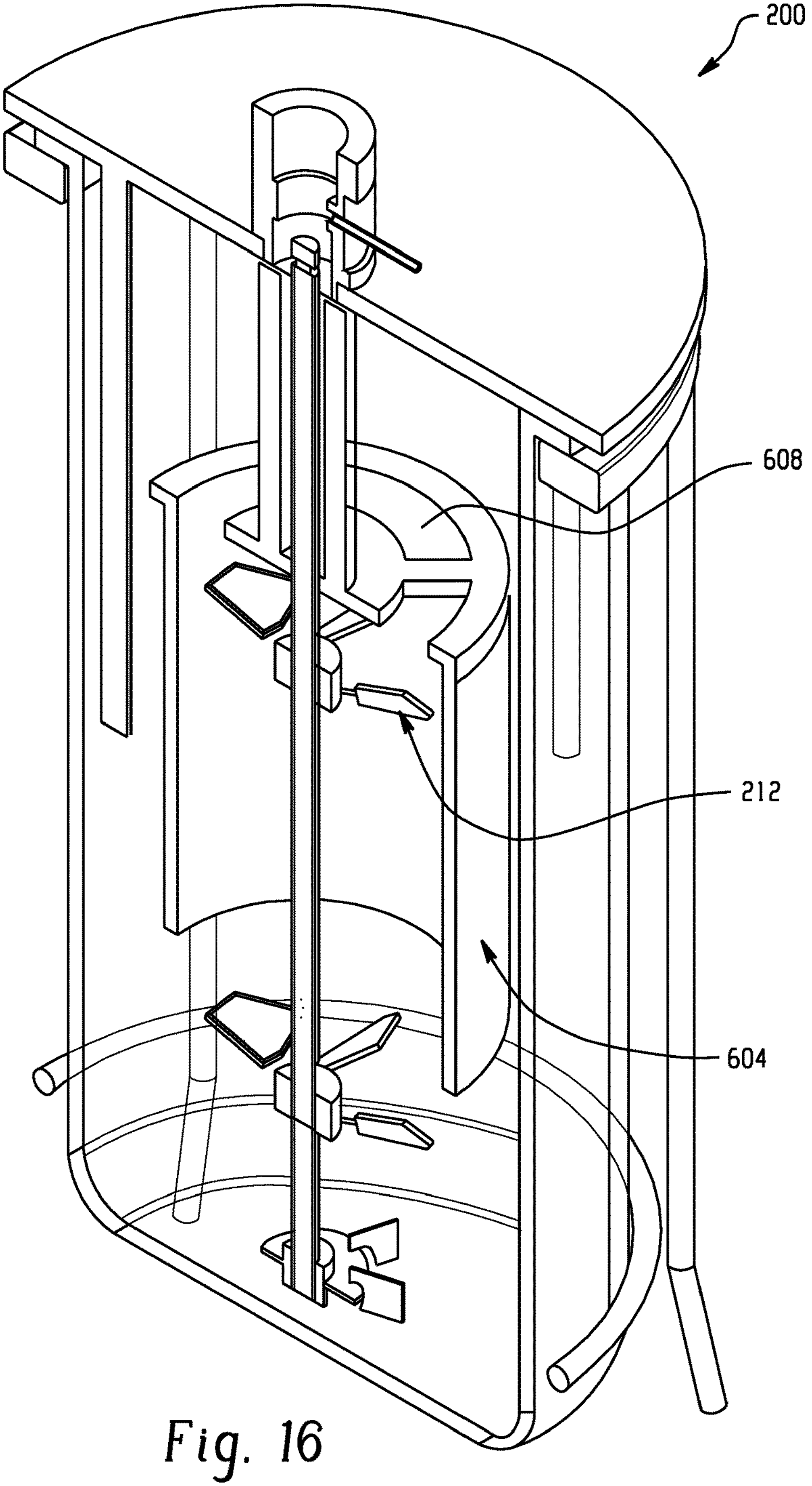

FIGS. 15 and 16 are cross-sectional side views of another exemplary fluid assembly.

Figure 17:
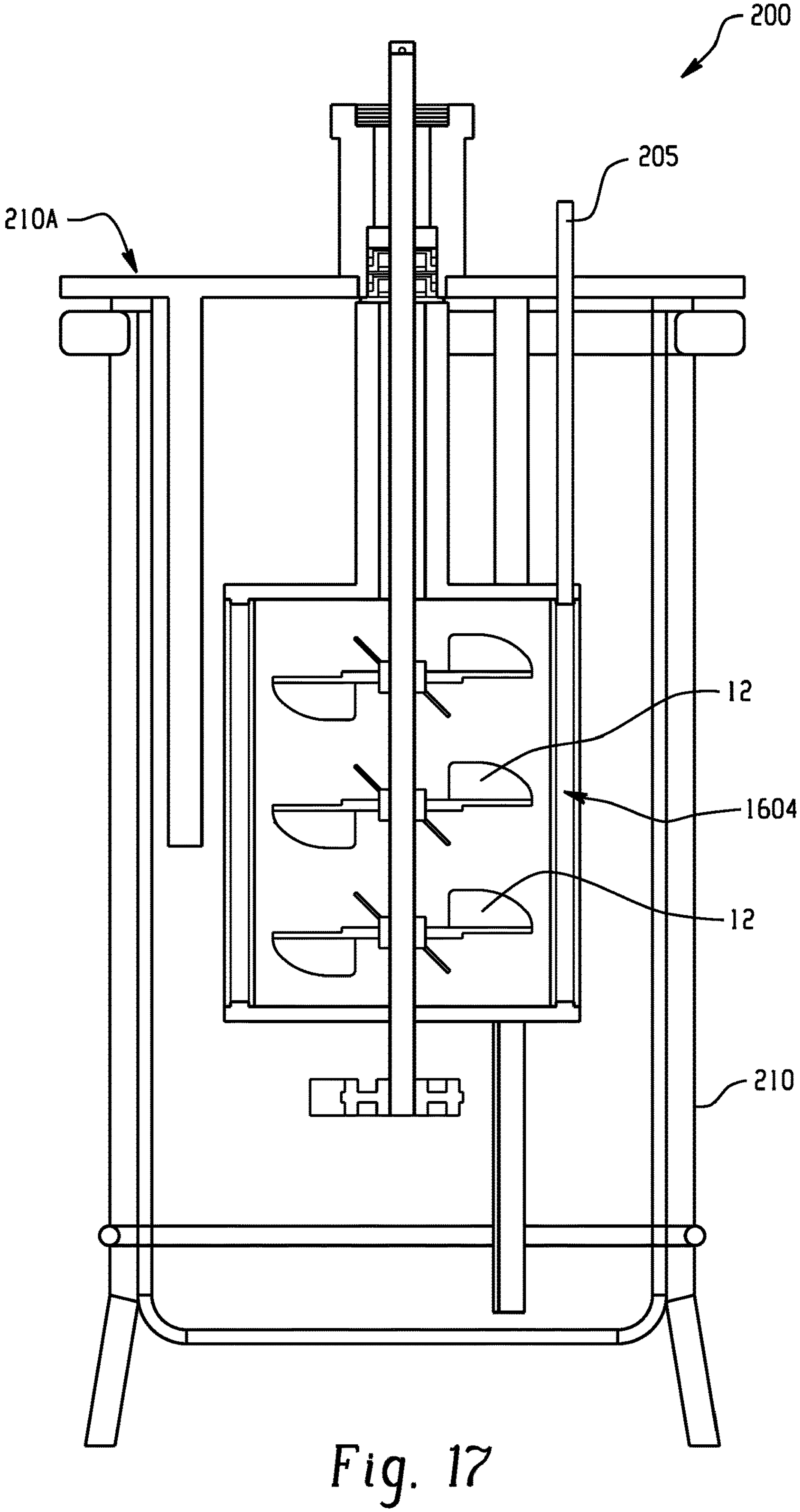
Figure 18:
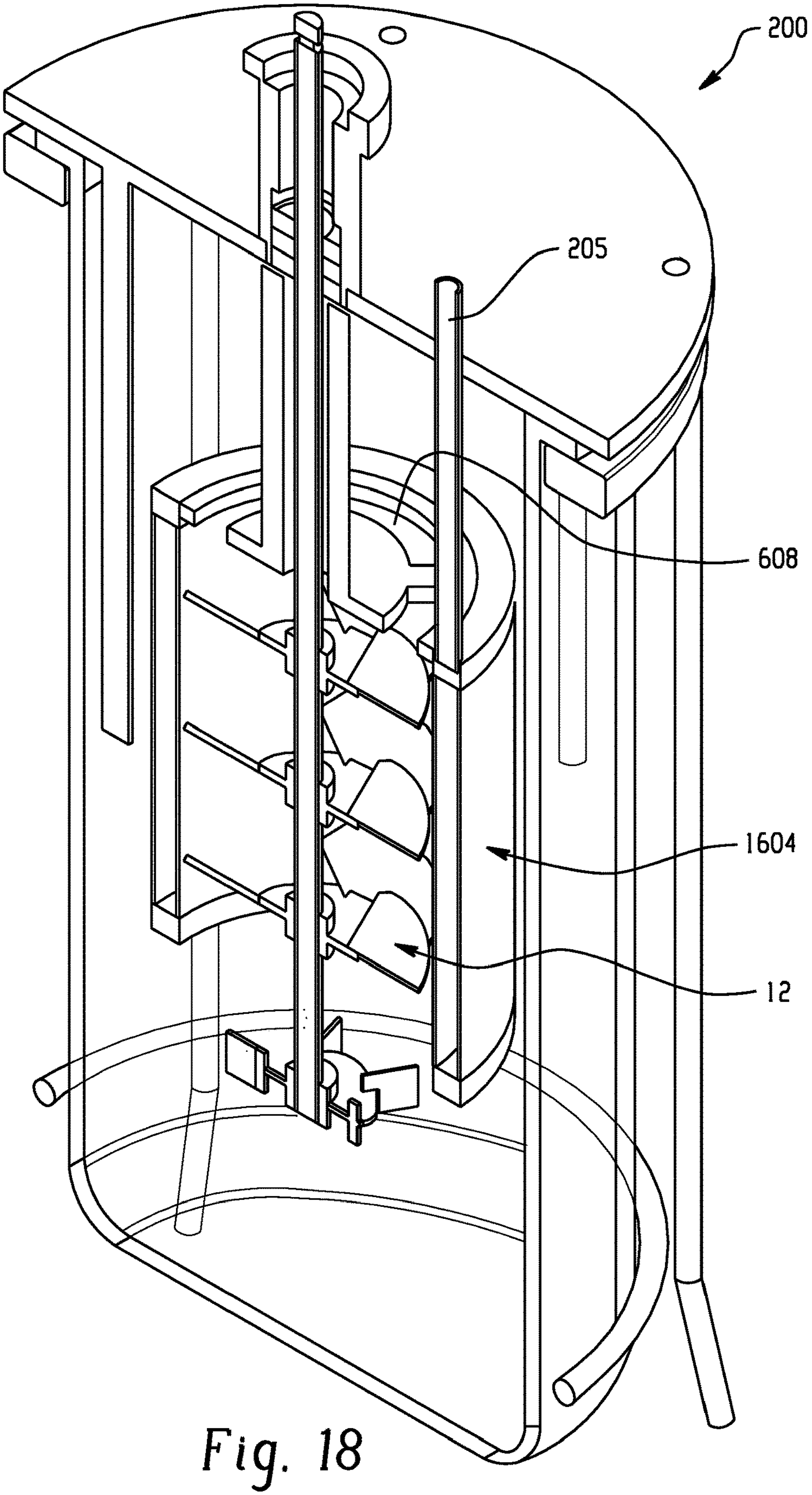

FIGS. 17 and 18 are cross-sectional side views of another exemplary fluid assembly.

Figure 19:
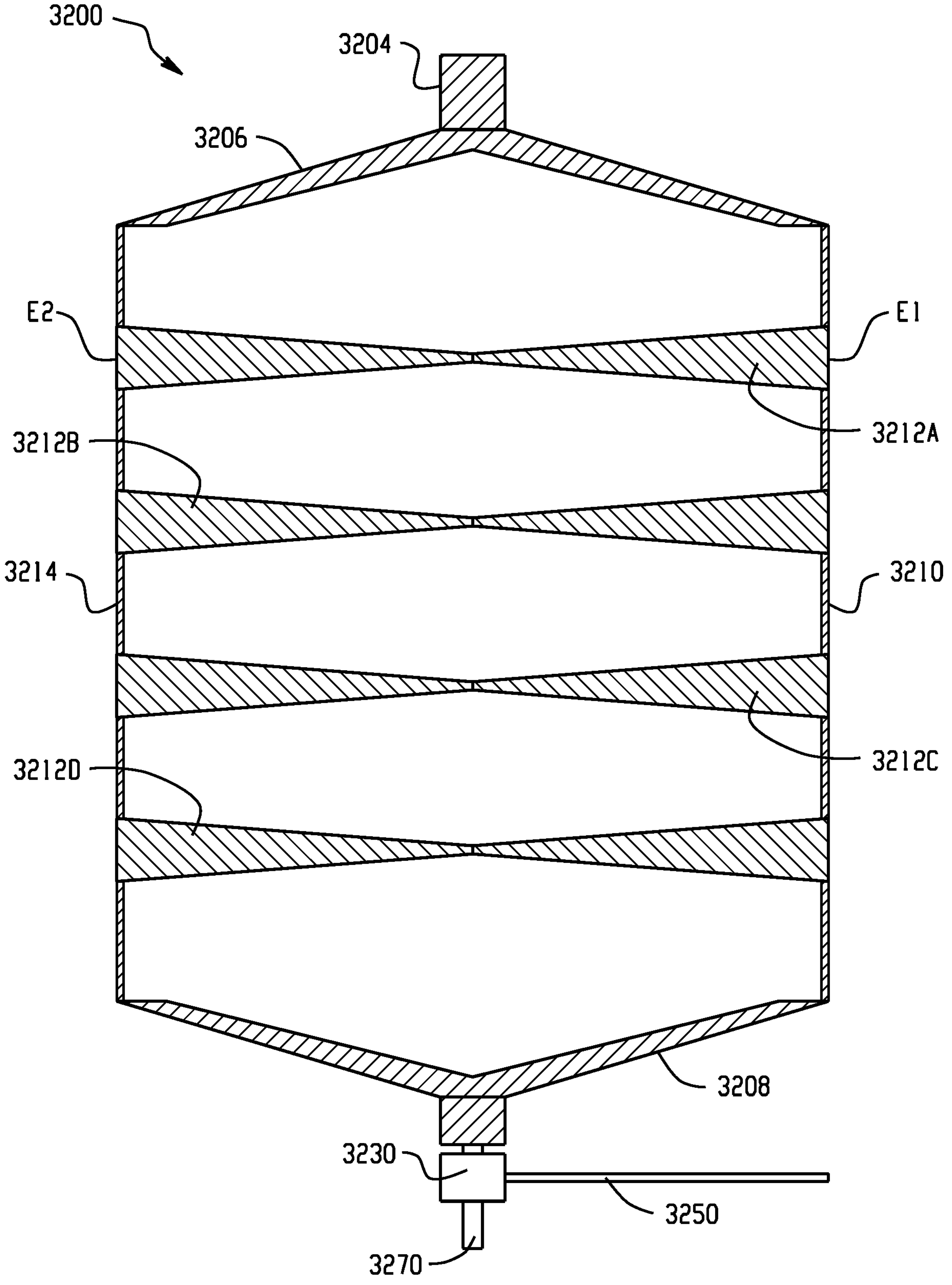

FIG. 19 is a side view of another exemplary fluid assembly.

Figure 20:
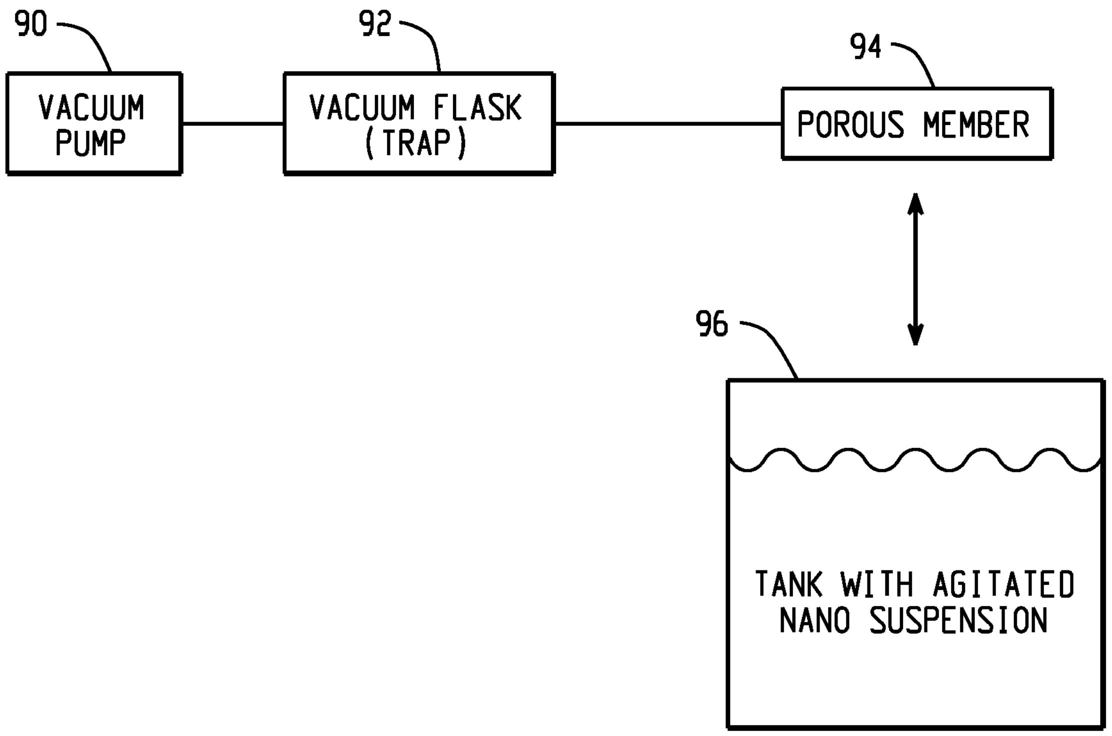

FIG. 20 depicts an experimental set up for creating a coating on a porous metal substrate.

DETAILED DESCRIPTION OF THE DISCLOSURE

The exemplary embodiments disclosed herein are illustrative of advantageous fluid assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary fluid assemblies and associated processes/techniques of fabrication/assembly and use are not to be interpreted as limiting, but merely as the basis for teaching one skilled in the art how to make and use the advantageous fluid assemblies and/or alternative assemblies of the present disclosure.

The present disclosure provides improved rotary interfaces for fluid assemblies (e.g., rotary interfaces for fluid flow in bioreactor applications), and related methods of fabrication and use.

More particularly, the present disclosure provides advantageous rotary interfaces for fluid flow through porous impellers for filtration and/or sparging for fluid assemblies (e.g., bioreactor applications), and related methods of fabrication and use.

As noted, some fluid assemblies or bioreactor assemblies used for processes such as fermentation are typically conducted in assemblies/reactors that include solid impellers and shafts. FIG. 1 is a schematic diagram of an example fluid or bioreactor assembly 100 that includes a solid impeller 112 and shaft 104A/104B. The bioreactor assembly 100 includes reactor walls of bioreactor 110 which hold reactants and by products (that are produced by reactions in the reactor assembly 100). The bioreactor 110 include an upper wall 110A that supports a secondary shaft housing 108, which is described below.

A motor 102 drives primary shaft 104A that contacts secondary shaft 104B via a quick-connect coupling 106. The quick connect coupling 106 permits rotary motion to be transferred from the motor 102 to the secondary shaft 104B via the primary shaft 104A. The primary and secondary shafts 104A and 104B are solid stainless steel shafts.

The secondary shaft 104B is in contact with the solid impeller 112, which is disposed in the bioreactor 110. The solid impeller 112 is not hollow and does not contain any pores that permit travel of a fluid through the impeller 112. A secondary shaft support housing 108 contains a bearing (which facilitate rotary motion of the shaft 104B) and seals (which prevent leakage of the reactants via the port that houses the shaft). The secondary shaft support housing 108 is seated atop the upper wall 110 of the bioreactor 110.

During normal use, when the bioreactor assembly 100 is setup up for a run, the components of and/or within the bioreactor 110 including the bioreactor 110, the bioreactor walls 110A and attached shafts/impellers 112 are cleaned and sterilized prior to use. After sterilization, the bioreaction products are placed into the bioreactor 110 and the external lines (e.g., pipes and tubes that discharge reactants into the bioreactor 110) along with the electric drive motor 102 are attached. The motor 102 cannot be sterilized which is why some bioreactor assemblies 100 commonly have the quick-connect coupling 106 and mounting mechanism for the drive motor 102 so it can be installed and removed when needed. This removal and installation of the motor 102, the shafts 104A/104B and impellers 112 is time consuming and laborious. Furthermore, the assembly 100 with the solid shafts 104A/104B and impellers 112 does not permit the bioreactor assembly 100 to be used for simultaneous reactions and filtering. These have to be conducted in separate steps and/or in separate devices.

It is therefore desirable to have a fluid assembly (e.g., bioreactor assembly) that can minimize cycle time loss and that can be used for multiple processes such as reaction and filtration without these operations having to be performed in separate steps.

In exemplary embodiments, the present disclosure provides for improved rotary interfaces for fluid flow through porous impellers for filtration and/or sparging for fluid assemblies (e.g., bioreactor applications), thereby providing significant operational, manufacturing and/or commercial advantages as a result, as discussed further below. It is noted that one skilled in the art will recognize that the ideas/embodiments presented herein for porous impellers/spargers are applicable to both batch and continuous ("perfusion") bioreactor or fluid assembly operating modes.

In example embodiments, disclosed herein is a fluid assembly (e.g., bioreactor) that includes a porous impeller which is in fluid communication with a hollow shaft that can be used to transport a reaction fluid to an external storage tank or the like. The fluid assembly or bioreactor can include a coupling mechanism that transmits rotary motion from a motor to a primary shaft and then to a hollow secondary shaft, while at the same time permitting removal of a filtrate from the fluid assembly or bioreactor via the hollow secondary shaft and a porous impeller. The coupling permits removal of the filtrate from the assembly/bioreactor while not having to dismantle the equipment. The coupling also permits removal of the filtrate from the assembly/bioreactor while not having to stop the impeller from rotating. In short, filtrate (which may include reactants, byproducts, products, and the like) may be removed from the assembly/bioreactor during operation without an interruption of the process (e.g., the rotation of the impeller does not have to be stopped or changed). Impeller position does not have to be changed either in order to extract the filtrate.

The present disclosure discloses a variety of methods where the filtrate can be extracted without changing impeller speed. In one embodiment, a primary shaft is offset from the secondary shaft (to which the impeller is attached) and the space between the two shafts is fitted with devices that can facilitate extraction of the filtrate. Rotary motion is transferred laterally and lateral movement of portions of the equipment/components may occur.

In another embodiment, the secondary shaft is provided with a rotary port that contacts a stationary rotary fitting into which the extract is fed. In this embodiment, there is no lateral transfer or rotary motion and there is no lateral movement of portions of the equipment. In yet another embodiment, the primary shaft and the secondary shaft are both hollow conduits through which filtrate may be extracted and fed to a storage tank or the like. In this embodiment too, there is no lateral transfer or rotary motion and there is no lateral movement of portions of the equipment. These embodiments are detailed with reference to respective figures below.

Referring now to the drawings, like parts are marked throughout the specification and drawings with the same reference numerals, respectively. Drawing figures are not necessarily to scale and in certain views, parts may have been exaggerated for purposes of clarity.

FIGS. 2 and 3 depict exemplary embodiments of a fluid assembly 200 (e.g., bioreactor assembly 200) where the primary shaft 204A (the shaft in direct contact with the motor 202) is offset from the secondary shaft 204B. The primary shaft 204A can detachably communicate with the secondary shaft 204B. In other words, the primary shaft 204A can be in operative communication with the secondary shaft 204B when desired, but this communication is reversible, e.g., it can be stopped when desired and reestablished when desired. This arrangement permits fluid to be extracted from the vessel/bioreactor 210 and to be transported to a storage tank or the like via a hollow secondary shaft 204B without stopping the reaction and/or agitation processes.

FIG. 2 depicts a coupling mechanism 400 that permits rotary motion from the motor 202 to be transferred via an idle shaft to the hollow second shaft 204B and the porous impeller 212. FIG. 2 depicts a schematic diagram of one exemplary embodiment of the fluid or bioreactor assembly 200 that comprises a vessel or bioreactor 210 in which is disposed a porous impeller 212. The porous impeller 212 is in fluid communication with a hollow secondary shaft 204B. The hollow secondary shaft 204B is in operative communication with a primary shaft 204A that is driven by a motor 202. In example embodiments, the motor 202 may be an electric motor, a pneumatic motor, a hydraulic motor, or a combination thereof.

Rotary motion generated by the motor 202 is transmitted to the porous impeller 212 via the primary shaft 204A, a coupling mechanism 400 and the secondary shaft 204B. The coupling mechanism 400 comprises an idler shaft 218 with a first gear 216A (or alternatively a first drive pulley 216A) and a second gear 216B (or alternatively a second drive pulley 216B) mounted thereon. The first gear 216A can mesh with first pulley 214A that is disposed on the primary shaft 204A, while the second gear 216B can mesh with second pulley 214B that is disposed on the secondary shaft 204B.

In an embodiment, if a first drive pulley 216A is used instead of the first gear 216A, then a belt may be used to transfer motion from the first pulley 214A mounted on primary shaft 204A, while a second drive pulley 216B may be used to transfer motion from the idling shaft 218 to the second pulley 214B. The coupling mechanism 400 can therefore transfer rotary motion from the motor 202 to the porous impeller 212 via the primary shaft 204A and the secondary shaft 204B.

In example embodiments, the secondary shaft 204B is a hollow shaft 204B while primary shaft 204A is a solid shaft. Fluid (housed/contained in the vessel/bioreactor 210) can be filtered into the porous impeller 212 and can be transported to a storage tank or the like via a pump or some other mechanism/means through the hollow portion of the secondary shaft 204B and hollow elbow 205. The elbow 205 may be fitted with seals and bearings (see FIG. 5 for description of the discharge conduit 220, which performs a similar function as the elbow 205) to permit the secondary shaft 204B to rotate while permitting the elbow 205 to stay stationary. The seals prevent leakage of the filtrate from the elbow 205. The elbow 205 can also be referred to as a discharge conduit (e.g., discharge conduit 220).

It is to be noted that the coupling mechanism 400 can be moved towards the motor 202 or away from it (as depicted by arrow 300). This movement towards the motor 202 and away from it may be used to facilitate decoupling of the motor 202 and primary shaft 204A from the secondary shaft 204B and porous impeller 212 (e.g., for cleaning and/or maintenance of the bioreactor assembly 200 and its components. Bearing box 208 includes or contains bearings that facilitate smooth rotary motion of the porous impeller 212. The bearing box 208 may also contain seals or the like that minimize leakage of reactants and products from the vessel/bioreactor 210.

FIG. 3 depicts another example embodiment of fluid or bioreactor assembly 200, where the motor 202 is offset to the side and the impeller shaft 204A is driven by the motor 202 with a single set of drive pulleys or gears. FIG. 3 is a schematic diagram that depicts another exemplary embodiment of the coupling mechanism 400 of the fluid/bioreactor assembly 200. In this embodiment, the motor 202 along with solid primary shaft 204A and first gear 214A (or alternatively first drive pulley 214A) can be moved towards or away from the hollow secondary shaft 204B upon which is mounted the second gear 214B (or alternatively second pulley 214B). As noted above, when the coupling mechanism 400 uses a drive pulley instead of gears, a belt is used to transmit motion from the motor 202 to the porous impeller 212.

In the FIG. 3 too, the secondary shaft 204B is a hollow shaft 204B while primary shaft 204A can be a solid shaft. Fluid (housed/contained in the vessel/bioreactor 210) can be filtered into the porous impeller 212 and can be transported to a storage tank or the like via a pump or mechanism/means through the hollow portion of the secondary shaft 204B and elbow 205. It is to be noted that the coupling mechanism 400 can be moved towards the motor 202 or away from the motor 202 (as depicted by arrow 300). This movement towards the motor 202 and away from it may be used to facilitate decoupling of the motor 202 and primary shaft 204A from the secondary shaft 204B and porous impeller 212 for cleaning and/or maintenance of the bioreactor assembly 200 and its components.

In certain embodiments, example methods of utilizing the bioreactor assemblies 200 depicted in FIGS. 2 and 3, it is noted that a fluid suitable for filtration can introduced or charged to the vessel/bioreactor 210. The fluid can be agitated with the porous impeller 212. The fluid can be filtered with the porous impeller 212 to create a filtrate. In example embodiments, the filtrate can be advantageously extracted from the fluid without changing the speed of the porous impeller 212 or without detaching the primary shaft 204A from the secondary shaft 204B.

FIG. 4 depicts another example embodiment of a fluid assembly 200 or bioreactor assembly 200 where fluid/filtrate can be transported from the porous impeller 212 to a discharge conduit 220 that is in fluid communication with a port in the secondary shaft 204B. In this embodiment, the primary shaft 204A and the secondary shaft 204B are in operative communication via the coupling mechanism 206, and there is substantially no lateral offset between the two shafts 204A, 204B. In other words, an axis of the primary shaft 204A can be substantially concentric with an axis of the secondary hollow shaft 204B, and rotary motion of the primary shaft 204A can be transferred directly to the secondary hollow shaft 204B without any lateral movement of moving parts or without any lateral transfer of rotary motion. The primary shaft 204A can be a solid shaft, while the secondary shaft 204B can be a hollow shaft 204B with the hollow portion being in fluid communication with the porous impeller 212. The secondary shaft 204B has a port 220A that is in fluid communication with the discharge conduit 220. Fluid/filtrate that is filtered through the porous impeller 212 (e.g., the filtrate) can be introduced or charged to a storage tank or the like via the hollow portion of the secondary shaft 204B, the port 220A and the discharge conduit 220. A pump or the like in fluid communication with the discharge conduit 220 and/or the storage tank facilitates introducing/charging the fluid/filtrate from the vessel/bioreactor 210 to the storage tank or the like.

As depicted in FIG. 4, the discharge conduit 220 can be secured to the secondary shaft 204B via a rotary fitting 222 (e.g., a tee 222). The rotary fitting 222 can be located above the vessel or bioreactor head plate/wall 210A or alternatively, below the vessel or bioreactor head plate/wall 210A, but above the fluid level in the vessel/bioreactor 210. The rotary fitting 222 can be provided with bearings 223 and seals 224. The bearings 223 permit the secondary shaft 204B to rotate in the rotary fitting 222 in order to agitate the contents of the vessel/bioreactor 210, while the seals 224 prevent fluid leakage from the vessel/bioreactor 210. A channel 225 can collect the filtrate emanating from port 220A, and can permit the filtrate to enter the discharge conduit 220 from where it is discharged to a storage tank or the like via a pump or other mechanism.

It is noted that an advantage of locating the rotary fitting 222 below the head plate/wall 210A is that a sterile barrier/seal may not be needed because below the head plate/wall 210A, both sides of the rotary fitting 222 (the inside and outside of the rotary fitting 222) would be sterile. When the rotary fitting 222 is located below the head plate/wall 210A it can be desirable that it does not leak and can operate continuously (e.g., at speeds up to 500 RPM).

In some embodiments, the rotary fitting 222 can be fabricated/manufactured from a material that does not substantially react with the reactants or byproducts of assembly 200. The rotary fitting may also not undergo bio-adhesion over time to reduce its efficacy. It can be desirable for the rotary fitting 222 to be fabricated from at least one of stainless steel, titanium, or a combination thereof; or to be fabricated from a metal and line-lined with a non-reactive material (e.g., glass or a polymer such as polytetrafluoroethylene (TEFLON) or polysiloxane or the like).

In an embodiment, in an example method of utilizing the bioreactor assembly 200 depicted in FIG. 4, a fluid suitable for filtration can be introduced or charged to the vessel/bioreactor 210. The fluid can be agitated with the porous impeller 212. The fluid can be filtered with the porous impeller 212 to create a filtrate. The filtrate can be extracted from the fluid without changing the speed of the porous impeller 212 or without detaching the primary shaft 204A from the secondary shaft 204B.

FIG. 5 depicts another example embodiment of a fluid assembly 200 or bioreactor assembly 200 where the filtrate from the bioreactor 200 may be extracted via the hollow impeller 212 and shafts (204A, 204B) during operation without any stoppage of the reaction or stoppage of the rotary motion of the shafts and impeller.

As depicted in FIG. 5, the primary shaft 204A and the secondary shaft 204B can both be hollow conduits 204A, 204B, which are in contact with the coupling mechanism 206. Rotary motion from the motor 202 can be transferred to the hollow secondary shaft 204B via hollow primary shaft 204A. A discharge conduit 220 located atop the hollow primary shaft 204A can be used to extract the filtrate from the vessel/bioreactor 210, via porous impeller 212. The discharge conduit 220 can be fitted with a bearing 223 and seals 224 which permit the discharge conduit 220 to remain stationary while the primary shaft 204A rotates. The seals 224 prevent fluid leakage.

In an embodiment, in an example method of utilizing the bioreactor assembly 200 depicted in FIG. 5, a fluid suitable for filtration can be introduced or charged to the vessel/bioreactor 210. The fluid can be agitated with the porous impeller 212. The fluid can be filtered with the porous impeller 212 to create a filtrate. The filtrate can be extracted from the fluid without changing the speed of the porous impeller 212 or without detaching the primary shaft 204A from the secondary shaft 204B.

As shown in FIG. 6, another example coupling mechanism 500 including elbow 205 (discharge tube 205) of example assembly 200 is now detailed below in conjunction with FIG. 6.

Shown in FIG. 6 is a schematic diagram of another example coupling mechanism 500 including elbow device 205 or discharge tube 205 designed to attach directly to fluid assembly 200 (e.g., assembly 200 for benchtop bioreactors). Coupling mechanism 500 having elbow 205 can be used for other assemblies/mixers as well. FIG. 6 depicts an example coupling mechanism 500 and does not show bearing supports (for ease of depiction) for the impeller shaft. FIG. 6 depicts a means to extract the fluid flowing through a hollow tube 204B via porous impeller 212.

The coupling mechanism 500 facilitates connecting a shaft with a discharge tube/conduit 205 and comprises a central hollow region for supporting a secondary hollow shaft 204B; the hollow region comprising a plurality of adapter plates 250 with o-ring seals 252 for the non-rotating surfaces, and lip seals 254 for the rotating secondary hollow shaft 204B to seal to the adapter plates 250; a central region situated between the adapter plates 250 that is in operative communication with an exit port 256 in the secondary hollow shaft 204B; the central region being operative to receive filtrate from a porous impeller 212 and to discharge it to the discharge conduit/tube 205; at least one connector disposed on at least one of the opposing sides of the adapter plates 250 to attach the coupling mechanism 500 to the bioreactor assembly 200. Details of attachment of the coupling mechanism 500 and device/tube 205 are shown in FIG. 6 and are detailed below.

It is noted that a mounting port for some bioreactor assemblies having mixing impellers utilize a port 258 having 30 mm threads 260. The coupling mechanism 500 associated with assembly 200 and as depicted in FIG. 6 can have a male (e.g., 30 mm) thread 260A on the bottom that screws directly onto the bioreactor head plate (210A). At the top of this coupling mechanism 500 is a female (e.g., 30 mm) thread 260B that a mixing agitator attaches to rather than connecting directly to the bioreactor head plate (210A). The impeller shaft (204) passes axially through this coupling mechanism 500 (through the longitudinal axis) and connects directly to the motor drive (202).

The impeller shaft (204) can have one or more holes that exist from the inner diameter (ID) to the outer diameter (OD) of the shaft at the center location of this coupling mechanism 500, allowing fluid flow through the shaft, out through the hole 256 in the center and exit through the tube 205 or hose barb connection 205 out the side of this coupling mechanism 500.

Inside the coupling mechanism 500 are a series of adapter plates 250 with o-ring seals 252 for the non-rotating surfaces and lip seals 254 for the rotating shaft to seal to these adapter plates 250 that are stationary. Some of the lip seals 254 are pointing upwards, and others downwards so that the coupling mechanism 500 will seal properly when the internal fluid is at positive pressures relative to its surrounding and at negative pressures relative to its surroundings. A spring positioned in the center can be there to keep the lip seals 254 in intimate contact with their sealing surfaces.

It is noted that some example porous impellers 212 (e.g., shown in FIGS. 2-7) can be fabricated/manufactured from a porous metal, a porous ceramic or a porous polymer. Porous metals can be preferred. Some example porous metals can include, without limitation, stainless steel, titanium, or a combination thereof. Porous ceramics can include, without limitation, glass, quartz, or a combination thereof. Porous polymers can include, without limitation, polyether ether ketone, polyether ketone, polyimides, polytetrafluoroethylene, polyfluoroethylenes, polyphenylene sulfides, polyolefins (e.g., polyethylene, polypropylene, or a combination thereof), or a combination thereof. These example polymers may be copolymerized with polysiloxanes if desired. Polysiloxane can impart non-stick properties as well as toughness to the polymers. Example polymers should be bio-inert, as well as be fabricated of a medical grade for use in the bioreactor assembly 200 or the like.

Example elastomer seals can be fabricated/constructed from FDA grade Viton or silicone rubber or other rubber compounds that are acceptable/suitable for pharmaceutical use and can survive repeated sterilizing procedures. It is noted that for some single use applications, (disposable) pharmaceutical grade polymers such as polyethylene or other lower cost polymers (such as those listed above) may be used if the cost of stainless steel is prohibitive.

FIG. 7 depicts another example embodiment of a porous impeller 212. Example porous impeller 212 includes a porous wall 404 that encompasses a hollow cavity 406. The porous wall 404 has pores effective to permit a desired filtrate into the hollow cavity 406. The porous wall 404 may have pores that are sized to permit a desired filtrate to enter the hollow cavity 406 while excluding other larger sized filtrate particles. The porous wall 404 contacts a wall 410 of the hollow secondary shaft 408. The hollow secondary shaft 408 is a conduit that has solid walls 410 that encompass a hollow passage 412 through which fluid from the hollow cavity 406 is transported. In other words, the hollow passage 412 is in fluid communication with the hollow cavity 406 in the porous impeller 212. Filtrate from vessel 210 collected in the hollow cavity 406 of the porous impeller 212 can thus be transported through the hollow passage 412 of the secondary shaft 408 (e.g., and to a storage tank or the like via an optional pump or other mechanism, as discussed above).

Some suitable impeller speeds for the bioreactor assemblies 200 of the present disclosure include rotational speeds of up to 5000 revolutions per minute (rpm). It is noted that some common speeds of rotation for the porous impeller 212 can vary between 0 and 500 revolutions per minute for some benchtop bioreactor assemblies 200 or the like. In some applications, the rotation speed can be much higher approaching speeds of 5000 rpm or the like. For higher speeds of rotation, external cooling of the bearings and/or sealing surfaces may be used to prevent overheating.

Some example fluid flow paths of the bioreactor assemblies 200 of the present disclosure (e.g., in FIGS. 2-7) can be designed for minimal pressure drops for fluids with viscosities in the range of 0.5 centipoise through 1000 centipoise. The fluids in some bioreactor assemblies 200 may be liquid, or a suspension of solids (live cell cultures) in a liquid with the percent of solids ranging from nearly zero up to the order of 60 volume percent. The inside diameter of the impeller shaft (204) can be on the order of 6 mm for benchtop bioreactor assemblies 200, and can be much larger for production scale reactor assemblies 200 that often approach thousands of liters in volume. It is noted that for some typical profusion bioreactor assembly 200 runs, the total fluid flow rate through the rotary device 212 can be very low for sampling (e.g., 0.1 or 0.2 bioreactor volumes per day (BVD), and up to three or four BVD's for production). In an example, for a small example benchtop reactor assembly 200 of around three liters working volume the lower end flow rate can be about 0.3 liters/day, and can be as high as twelve liters/day. In some embodiments, as the working volume of the reactor assembly 200 increases, so does the fluid flow rate.

As noted above, the designs of the example fluid assemblies 200 or bioreactor assemblies 200 disclosed herein are advantageous in that they permit filtrate extraction without changing the speed of the porous impeller 212, and without dismantling equipment. This can advantageously reduce cycle time. Moreover, because the equipment can be dismantled easily when maintenance is desired, downtime and/or costs can be reduced.

FIG. 8 is a side view schematic of an example hollow rotating shaft 204B and at least one impeller blade 213 of porous impeller 212, the at least one impeller blade 213 angled/oriented relative to a horizontal plane/surface H (e.g., angled/oriented at 45 degrees with respect to a horizontal plane/surface H of a bottom surface of the shaft 204B).

As shown in FIG. 8, the porous impeller 212 includes at least one porous impeller blade 213 (e.g., two or more porous impeller blades 213), with each porous impeller blade 213 connected to a vertically oriented, hollow, rotating shaft 204B (e.g., shaft 204B configured to be positioned/located in a vessel/tank 210 and which agitates/filters a fluid/liquid volume of the vessel/tank 210, as described above in connection with assemblies 200 of FIGS. 2-7). Each at least one porous impeller blade 213 comprises an outer shell 215, at least a portion of which is porous, and an internal cavity 217 which is contiguous to the hollow space of the rotating hollow shaft 204B. Each at least one blade 213 on the first porous impeller 213 can be angled/oriented with respect to a horizontal plane/surface H at a first angle (e.g., angled/oriented at 45 degrees with respect to a horizontal plane/surface H of a bottom surface of the shaft 204B).

FIG. 9 is a side view schematic of an example hollow rotating shaft 204B and two impellers 1212A and 1212B, with a first impeller 1212A having at least one blade 1213A angled/oriented relative to a horizontal plane/surface H (e.g., angled/oriented at 45 degrees with respect to a horizontal plane/surface H of a bottom surface of the shaft 204B), and a second impeller 1212B having at least one blade 1213B angled/oriented relative to a horizontal plane/surface H (e.g., angled/oriented at 30 degrees with respect to a horizontal plane/surface H of a bottom surface of the shaft 204B).

Similar to FIG. 8 and as shown in FIG. 9, a first porous impeller 1212A includes at least one porous impeller blade 1213A (e.g., two or more porous impeller blades 1213A), with each porous impeller blade 1213A connected to a vertically oriented, hollow, rotating shaft 204B (e.g., shaft 204B configured to be positioned/located in a vessel/tank 210 and which agitates/filters a fluid/liquid volume of the vessel/tank 210, as described above in connection with assemblies 200 of FIGS. 2-7). Each at least one porous impeller blade 1213A comprises an outer shell 1215A, at least a portion of which is porous, and an internal cavity 1217A which is contiguous to the hollow space of the rotating hollow shaft 204B. Each at least one blade 1213A on the first porous impeller 1212A can be angled/oriented with respect to a horizontal plane/surface at a first angle (e.g., angled/oriented at 45 degrees with respect to a horizontal plane/surface H of a bottom surface of the shaft 204B).

As shown in FIG. 9, a second porous impeller 1212B includes at least one porous impeller blade 1213B (e.g., two or more porous impeller blades 1213B), with each porous impeller blade 1213B connected to a vertically oriented, hollow, rotating shaft 204B (e.g., shaft 204B configured to be positioned/located in a vessel/tank 210 and which agitates/filters a fluid/liquid volume of the vessel/tank 210, as described above in connection with assemblies 200 of FIGS. 2-7). Each at least one porous impeller blade 1213B comprises an outer shell 1215B, at least a portion of which is porous, and an internal cavity 1217B which is contiguous to the hollow space of the rotating hollow shaft 204B. Each at least one blade 1213B on the second porous impeller 1212B can be angled/oriented with respect to a horizontal plane/surface H at a second angle (e.g., angled/oriented at 30 degrees with respect to a horizontal plane/surface H of a bottom surface of the shaft 204B).

The second porous impeller 1212B can be positioned/located on the hollow shaft 204B at the same or different positions/locations along the length of the shaft 204B as the first porous impeller 1212A. Each blade 1213B on the second impeller 1212B can be angled/oriented at a second angle with respect to the horizontal plane surface H that differs from the first angle of blades 1213A. In an example embodiment, the second angle (e.g., 30 degrees) is lower (more acute) than the first angle (e.g., 45 degrees).

As such, it is noted that the present disclosure provides for configurations of impellers (e.g., impellers 212, 1212A, 1212B of FIGS. 8 and 9) for filtration within a vessel/tank (e.g., vessel/tank 210) in conjunction with agitation, and methods for operating the example impellers (e.g., impellers 212, 1212A, 1212B of FIGS. 8 and 9). As noted and in an example embodiment, a first porous impeller 1212A with two or more blades 1213A set at a preferred angle for agitation, e.g., 45°, can be used in conjunction with a second porous impeller 1212B with two or more blades 1213B and blade angles set to minimize the amount of accumulated material in the form of a filter cake. As the filtration progresses, the blades 1213A of the first impeller 1212A may accumulate a filter cake, and the first impeller 1212A may therefore lose its effectiveness as a filter while still providing adequate agitation. However, the second impeller 1212B may not accumulate a filter cake as quickly as the first impeller 1212A because of the chosen angle of the blades 1213B on the second impeller 1212B, and will therefore become the primary filtration mechanism as the filtration progresses (e.g., for assembly 200). In some embodiments, the angle of the blades 1213B in the second impeller 1212B may be set to an angle of 0 degrees, or completely horizontal with horizontal plane/surface H in an extreme case.

In certain embodiments, it is noted that the first porous impeller 1212A (or 212) includes an outer surface 1215, the outer surface 1215A substantially porous throughout the outer surface 1215A of the first porous impeller 1212A. In other embodiments, the first porous impeller 1212A (or 212, or 1212B) includes an outer surface 1215A, the outer surface 1215A porous at pre-determined locations of the outer surface 1215A of the first porous impeller 1212A.

Another embodiment, as discussed further below, is a configuration in which the individual blades of the impeller are replaced with a single, contiguous body. An example form of this is a disk, however other shapes could be envisaged such as a wheel with radial spokes that accommodate the permeate flow to the shaft (204B). Preferably, the porous region of the rotating disk or body may be located some distance from the shaft (204B) to provide the high shear required to remove accumulated filter cake, as discussed further below.

The present disclosure provides a number of designs related to the concept of combining agitation of a vessel/tank (210) with filtration by means of one or more porous impellers (e.g., impellers 212, 1212A, 1212B) connected to a rotating hollow shaft (204B) through which filtrate liquid (permeate) is withdrawn. In an example embodiment and as discussed further below, the present disclosure provides for the concept of a rotating porous filter that need not be a primary or secondary agitation device. Such embodiments can be particularly applicable to the field of bioreactors and cell growth in bioreactors, particularly those in which pharmaceutical products are desired; however, these embodiments/concepts are generally applicable to any stirred vessel/tank in which it may be advantageous to perform internal filtration simultaneously with filtered liquid (permeate) withdrawal.

In an embodiment/application, a pressure gradient between the interior of the vessel/tank (e.g., vessel/tank 210) and the interior of the rotating hollow shaft (e.g., shaft 204B) drives fluid/liquid flow through the porous shells of the one or more porous impellers (e.g., impellers 212, 1212A, 1212B). The fluid/liquid passes through the porous shells of the impellers into the internal cavity of each porous impeller blade and further into the hollow shaft (204B); at least a portion of any suspended solids in the fluid/liquid are filtered by the porous outer shells and do not pass into the internal cavities or hollow shaft (204B). In use, it is noted that a filter cake may form on the exterior of the impeller blades comprising accumulated filtered solid materials. Certain example embodiments of the present disclosure provide for a reduction of the severity and effects of the accumulated filter cake on tank filtration.

In another embodiment, a first angle of the blades 1213A of the first porous impeller 1212A with respect to the horizontal H is chosen to maximize mixing efficiency of the fluid/liquid contents of the tank (210); and in which the second angle of the blades 1213B of the second porous impeller 1212B with respect to the horizontal H is chosen to minimize or at least substantially reduce the rate of accumulation of filtered solid materials relative to that sustained by the first impeller 1212A, where substantial reduction is defined as by at least 50%. In this embodiment/context, mixing efficiency may be determined by many metrics, but shall include the overall liquid-side mass transfer rate of any gas phase species introduced into the fluid/liquid as a gas, a portion of which is dissolved and transported within the fluid/liquid of the vessel/tank.

In an application according to this embodiment, the first porous impeller 1212A provides the primary mixing means of the fluid/liquid volume within the tank (210). As a filter cake accumulates on the first impeller 1212A, the agitation it imparts is not substantially diminished. A filter cake also accumulates on the second impeller 1212B, but at a much lower rate than on the first impeller 1212A. As the filter cake accumulates on first porous impeller 1212A and less so on the second porous impeller 1212B, the second impeller 1212B becomes the primary filtration means (e.g., of assembly 200). At the point at which the first porous impeller 1212A is no longer filtering a significant amount of fluid/liquid because its filter cake prevents fluid/liquid substantially to pass through, the second porous impeller 1212B will provide substantially all of the filtering capability. The advantage of this embodiment over the case of a single porous impeller (212 or 1212A) operating at a first angle alone is that the addition of the second impeller 1212B operating at the second blade 1213B angle will have the effect of extending the duration of a campaign of simultaneous agitation and filtration without stopping the process to clean or replace the first porous impeller 1212B.

Taken to an extreme, the second angle of the blades 1213B of the second impeller 1212B may be 0 degrees with respect to the horizontal plane/surface H as shown in FIG. 10. This can have the effect of maximizing the lateral shear on the surface of the blades 1213B of the second impeller 1212B to minimize filter cake formation.

In an example embodiment and as shown in FIGS. 12 and 13, the blades of the second porous impeller (e.g., blades 1213B of FIG. 11) are replaced by a single contiguous rotating porous body 2212B that is used as the primary filtration means for the assembly/system (200). A first impeller 2212A with impeller blades 2213A oriented at a first angle with respect to the horizontal H is attached to a hollow rotating shaft (204B), and a contiguous rotating porous body 2212B is connected to the hollow rotating shaft (204B). It is noted that the blades 2213A of the first impeller 2212A may or may not be porous. The contiguous porous body 2212B comprises a porous outer shell 2215B and a hollow interior cavity 2217B that is in fluid communication with the interior of the hollow rotating shaft (204B). In a preferred embodiment, the blades 2213A of the first impeller 2212A are oriented at 45° with respect to the horizontal H, and the contiguous rotating porous body 2212B takes the form of a disk, as shown in FIGS. 12 and 13. In a further preferred embodiment, the first impeller 2212A is of conventional design. The porous regions on the rotating contiguous body 22112B can advantageously be placed or positioned a minimum distance from the shaft 204B to ensure that they are in regions of high lateral shear to maximize removal of any accumulated filter cake.

In use, the first impeller 2212A may be of a conventional (non-filtering) design optimized for agitation of the fluid/liquid volume of the tank 210, while one or more rotating contiguous bodies 2212B may be added to the hollow rotating shaft 204B to provide the necessary filtration area. The advantage of the disk geometry is that fluid flow is well-characterized in flow over a rotating disk (2212B), and a horizontal rotating disk 2212B will provide relatively little drag force, thus ensuring high mixing efficiency (low power numbers) overall for the assembly/system (200). The contiguous body 2212B has the further advantage that it may comprise more surface area for filtration than a series of discrete blades. The contiguous body 2212B can take several forms in addition to a disk, including a spoked wheel, a saucer shape (e.g., in which the contiguous body near the hollow shaft is thicker than that near the edges), and/or continuous wheel which features a rounded edge like a bicycle tire (e.g., when oriented horizontally).

FIG. 14 is a side view of another exemplary fluid assembly 200. A head plate 210A can be positioned at a top portion of the vessel 210. At least a portion of the discharge conduit 205 can be positioned below the head plate 210A. A seal can be positioned below the head plate 210A.

As shown in FIG. 14, assembly 200 can be utilized for filtration and/or sparging through porous mixing impellers 212 having propeller blades. The assembly includes a hollow tube shaft 204 between the impeller blades of the impellers 212 and the coupling mechanism 500 (e.g., rotary fluid coupling mechanism 500), with the coupling mechanism 500 beneath the bioreactor headplate 210A, and a fluid path from the coupling mechanism 500 through the head plate 210A, and installation of the porous impeller blade assemblies(s) 212 to the hollow shaft 204 for filtration and/or sparging, as discussed.

As shown in FIG. 14, the rotary fluid extraction mechanism 500 is mounted below the head plate 210A. A reason for this can be for better reliability in terms of maintaining a sterile barrier for assembly 200. With the rotary feedthrough 500 being below the headplate 210A, if one of the rotary shaft seals was to leak, one would not lose sterility, as both sides of the coupling 500 are within the sterile region of the reactor vessel 210 and if assembly 200 has a leak. If the rotary feedthrough mechanism 500 is mounded above the head plate 210A and there is a leak, the sterile barrier can be broken, and there can be potential for a spill onto the benchtop or wherever the reactor assembly 200 is located.

FIGS. 15 and 16 are cross-sectional side views of another exemplary fluid assembly 200.

Assembly 200 of FIGS. 15 and 16 is configured to support filtration and/or sparging through porous mixing impellers 212 having propeller blades. A housing 604 (e.g., inverted cup housing 604) surrounds at least a portion of the impeller blades of impellers 212 to create pressure on the blades of impellers 212 to promote fluid flow through the porous blades and/or porous impellers 212, and out the fluid extraction port 205. In some embodiments, the shaft 204 and rotary fluid coupling can be mounted above the head plate 210A. In some embodiments, both impeller assemblies 212 can be positioned/located substantially within the inverted cup housing 604.

The top of the inverted cup housing 604 can have (small) openings or apertures 608 to restrict the upward flow of the fluid driven by the impeller(s) 212, which creates a localized pressure increase around the impellers 212. This increased localized pressure can create a differential pressure between the outside and interior if the porous blades of impellers 212 and the fluid will pass through the blades of impellers 212 and flow upwards up the hollow stirring shaft 204 and exit the bio reactor vessel 210. One intent here is to perform filtration without the need for an external pump to induce fluid flow through the porous impellers 212 (e.g., having blade filters). This reduces the complexity of the assembly/system 200 and reduces the chances of contamination and loss of sterility from an external pump or the like.

It is noted that FIGS. 15 and 16 are not to scale, and the distance between the porous impeller blades of impellers 212 and the inverted cup housing 604 can be much smaller than depicted to get the needed pressure differential to induce fluid flow through the porous media 212 when the impeller blades are rotating.

In addition, the size of the openings 608 at the top of the inverted cup housing 604 may need to be smaller, and with the possibility of the addition of deflectors or the like to direct the fluid flow passing through these openings 608 to achieve better fluid mixing within the reactor 210, and/or to control the flow of fluid to minimize dead spots withing the bioreactor vessel 210.

FIGS. 17 and 18 are cross-sectional side views of another exemplary fluid assembly 200.

FIGS. 17 and 18 depict views of an example bioreactor assembly 200 configured to support filtration through a porous housing 1604 surrounding one or more standard mixing impeller(s) 12. The housing 1604 can have a similar shape as housing 604 described above, and it is this housing 1604 that performs the filtration. When the impeller/propeller blades 12 rotate and drive fluid upwards and out the restrictive passages/openings 608 at the top of the inverted cup shaped filter housing 1604, a localized pressure is created withing the housing 1604. The housing 1604 can include a hollow tube geometry with at least a portion of the internal surface of the tube 1604 being porous, and the exterior surface of the tube 1604 being substantially solid, and an internal void volume that separates the outer diameter (OD) from the inner diameter (ID). A fluid flow tube 205 connects the void space within the housing 1604 to the head plate 210A for a fluid path for filtered liquid (filtrate) to leave the bioreactor vessel 210. In some embodiments, the impeller blades 12 can be solid and no modification to the stirring shaft or blades may be required other than their relative mounting locations on the stirring shaft. In other embodiments, at least some portions of blades and/or impellers 12 are porous.

The top of the inverted cup filter housing 1604 has (smaller) openings 608 to restrict the upward flow of the fluid driven by the impeller(s) 12 which will create a localized pressure within the filter housing 1604. This increased localized pressure can create a differential pressure between the ID and interior volume space of the filter housing 1604, inducing fluid flow through the porous media on the ID surface of the housing 1604, and then through the tube 205 and exiting through the fluid extraction port 205 on the head plate 210A. An intent here is to perform filtration without the need for an external pump to induce fluid flow through the porous filter housing 1604. This can reduce the complexity of the assembly/system 200, and can reduce the chances of contamination and loss of sterility from an external pump or the like. The rotation of the blades 12 withing the filter housing 1604 can create fluid motion across the filter surface and reduce or eliminate cake formation of the porous media 1604, leading to longer filtration life before filter plugging/fouling.

FIGS. 17 and 18 are not necessarily to scale, and the distance between the impeller blades 12 and the inverted cup filter housing 1604 can be much smaller than depicted to get the needed pressure differential to induce fluid flow through the porous media 1604 when the impeller blades 12 are rotating.

In addition, the size of the openings 608 at the top of the inverted cup filter housing 1604 may need to be smaller, and with the possible addition of deflectors to direct the fluid flow passing through these openings 608 to achieve better fluid mixing within the reactor vessel 210, and/or to control the flow of fluid to minimize dead spots withing the bioreactor vessel 210.

For the assemblies 200 illustrated and described in FIGS. 15-18, one can either have porous impeller blades 212 or a porous housing 1604 surrounding the impellers 12 for filtration. It is noted that both the impellers 12, 212 and the filter housings 604, 1604 surrounding the impellers 12, 212 can be at least partially porous for additional filtration areas.

For the assemblies 200 in at least FIGS. 14-18, the porous media (e.g., 212, 1604) can be fabricated from any material suitable of biopharmaceutical use (e.g., stainless steel, glass, plastic, etc.) or the like. The thickness, area of the porous media, and the pore size of the media can be adjusted to satisfy the strength requirement and filtration efficiencies needed for the bioreactor operations of assemblies 200.

In other embodiments and as shown in FIG. 19, the present disclosure provides for a fluid assembly or bioreactor assembly 3200 (e.g., assembly 3200 for single use bag reactors or the like). In some embodiments, the fluid assembly 3200 takes the form of a ladder/rung style porous mixer-filter assembly 3200 for bioreactors or the like (e.g., for single use bag reactors), as described further below.

Example fluid assembly 3200 includes a shaft 3204 having an upper manifold 3206 and a lower manifold 3208, the upper manifold 3206 mounted with respect to the lower manifold 3208 by a first side member 3210 and a second side member 3214, and at least one porous impeller 3212A (e.g., four impellers 3212A to 3212D) mounted with respect to the first and second side members 3210, 3214.

At least a second porous impeller 3212B can also be mounted with respect to the first and second side members 3210, 33214. The second porous impeller 3212B can be configured to be positioned at a different elevational position than the first porous impeller 3212A within the vessel defined by first and second side members 3210, 3214.

In some embodiments, the first and second side members 3210, 3214 can comprise flexible ropes or the like.

A first exterior edge E1 of the first porous impeller 3212A can be connected to the first side member 3210, and a second exterior edge E2 of the first porous impeller 3212A can be connected to the second side member 3214. Impellers 3212B-D can be connected similarly to members 3210, 3214.

Filtrate from the fluid housed in the vessel defined by first and second side members 3210, 3214 can be extracted from the vessel via at least the first porous impeller 3212A, the porous or hollow first and second side members 3210, 3214 and the porous/hollow lower manifold 3208. Manifold 3208 can be porous if additional filtration area is needed.

The lower manifold 3208 can be mounted with respect to a rotary fluid port 3230. The port 3230 can be in communication with a tube 3250 or the like, thereby allowing flow from the rotary fluid port 3230 (e.g., to an external port on a bag).

The first and second side members 3210, 3214 can provide a fluid flow path from the porous impellers 3212A, etc. down to the rotary fluid port 3230 (and exiting through a reactor bag).

In use, exemplary assembly 3200 utilizes a ladder/rung design where flexible ropes of members 3210, 3214 are connected to the exterior edges of impellers 3212A, etc., and the ladder/rung design of the flexible ropes of members 3210, 3214 is rotated (driven at the top via upper manifold 3206 and shaft 3204), and with the lower manifold 3208 also rotating and attached to the bottom via a pivot bearing 3270. The entire assembly 3200 can be under tension once a bag is filled with fluid. Depending on the size of the bioreactor, multiple mixing impellers 3212A, etc. at different elevations within the reactor vessel can be employed to provide the proper mixing needed.

As such, assembly 3200 provides that the upper manifold 3206 can connect directly to the rotary drive mechanism of the reactor (e.g., shaft 3204). Suspended below the upper manifold 3206 are one or more porous mixing impellers 3212A, etc. connected to the manifolds 3206, 3208 via flexible tubing members 3210, 3214, thereby providing a fluid flow path downwards. Near the bottom of the reactor is a lower manifold 3208 that is connected to the bottom of the reactor through a pivot bearing 3270 and a rotary fluid port 3230 with a flexible tube 3250 connected from the rotary port 3230 to an exterior port at or near the bottom of the bag reactor for the filtrate to exit the reactor.

When a bag is installed into the reactor vessel and filled with fluid, the bag expands and the entire assembly 3200 is under slight tension so that when the top manifold 3206 is rotated by the motor drive (via 3204), the entire assembly (except for the rotary fluid port 3230 at the bottom) rotates with it.

The porous blades of impellers 3212A-D can be of a variety of shapes (e.g., rectangles rotated to 45 degrees or other angles; rectangular blades twisted such that the pitch is near vertical at the edges and horizontal at the center; or any other shape that provides adequate mixing while rotating and having enough surface area to provide filtration at the flow rate needed for such applications).

In some applications of assembly 3200, the permeate flow rate desired can be around one to two bioreactor volumes/day if the impeller 3212 filters are the only filtration system installed. In cases where the impeller 3212 filters are designed to be a pre filter for a subsequent external filter, the flow rate through filtration assembly 3200 can be significantly higher, being closer to ten to twenty bioreactor volumes per day.

For such designs, a preferred material of construction can be polymeric so that gamma irradiation can be utilized to sterilize the parts of or the entire assembly 3200 after installation into the bag. Any polymeric material compatible to standard bioreactor processes can be used (e.g., polyethylene, polypropylene, etc.).

Table 1 below shows results from filtration performance evaluations using baker's yeast and utilizing certain example porous impellers of the present disclosure, at low concentrations solids filtration. In Table 1, Equiv. MG represents the Equivalent Media Grade of each example porous impeller tested. It is noted that the MG is approximately the average pore diameter in microns.

TABLE 1

| Equiv. MG | L Flow ml/min | Clarity NTU | Capture % | # Samples Tested |
|---|---|---|---|---|
| 0.0 | 0.0 | 0.228 | 100 | 0 |
| 2 | 2.5 | 5.4 | 98.6 | 1 |
| 5 | 5.8 | 13.4 | 96.5 | 4 |
| 7 | 17.4 | 44.1 | 88.5 | 2 |
| 10 | 209 | 349 | 9.5 | 2 |

Table 2 below shows results from filtration performance evaluations using baker's yeast and utilizing certain example porous impellers of the present disclosure, at high concentrations solids filtration. In Table 2, Equiv. MG represents the Equivalent Media Grade of each example porous impeller tested. Again, it is noted that the MG is approximately the average pore diameter in microns.

TABLE 2

| High Concentration | | | | |
|---|---|---|---|---|
| Equiv. MG | L Flow ml/min | Clarity NTU | Capture %* | # Samples Tested |
| 0.0 | 0.0 | 0.228 | 100 | 0 |
| 2 | 1.3 | 19.3 | 99.4 | 1 |
| 5 | 1.7 | 74.9 | 97.6 | 4 |
| 7 | 3.4 | 212.9 | 93.1 | 5 |
| 10 | 5 | 2852 | 8.0 | 4 |

Table 3 below shows results from filtration performance evaluations using baker's yeast and utilizing certain example porous impellers of the present disclosure, and for filtrate flow and capture efficiency testing using baker's yeast.

TABLE 3

| | | Bubble Pt | Equivalent | N2 Gas Flow | Filtrate Flow (ml/min) | | | | Filtrate Clarity (NTU) | | | |
|---|---|---|---|---|---|---|---|---|---|---|---|---|
| Set # | Blade # | ("Hg) | Media Grade | @ 5 PSI (SLM) | 6' Hg | 8' Hg | 10' Hg | 12' Hg | 6' Hg | 8' Hg | 10' Hg | 12' Hg |
| 1 | 1 | 2.09 | 1 | 7.40 | 8.5 | 9.5 | 11.9 | 14.6 | 4.4 | 4.4 | 4.5 | 6.5 |
| | 2 | 2.09 | 1 | 7.42 | | | | | | | | |
| | 3 | 2.21 | 1 | 5.70 | | | | | | | | |
| | 4 | 2.09 | 1 | 6.47 | | | | | | | | |

The present disclosure also provides for coated porous members (e.g., coated porous impellers; coated porous sparging members; coated porous metal members), methods of manufacture thereof, and articles comprising of the same. In particular, this disclosure relates to powder-based coatings on porous metal members (e.g., porous impellers; porous spargers) for improved biofouling resistance and performance in fluid assemblies (e.g., bioreactor assemblies).

It is noted that porous media can be employed to enhance interfacial mass transfer of components of a fluidic or solid phase into another fluidic phase. For example, during a sparging process, air is flowed through a porous metal tube that is submerged in water. The air forms bubbles that will travel in the water after leaving the surface of the sparger. At the interface between the air bubble and the water, oxygen will transfer into the water. This technique is often used in bioprocessing industries to introduce oxygen, carbon dioxide, or other chemicals into a liquid solution, which is not limited to water. A common issue with the state-of-the-art technology in the sparging field is that the bubbles coming off of the sparger can introduce turbulence and shearing forces due to bubble coalescence, which can damage the product in a bioreactor tank. Secondly, the organic matter in the bioreactor tank can lead to fouling of the porous sparger, as the matter will adhere to the rough, porous surface of the sparger's porous media.

It is therefore desirable to develop a method of coating a porous metal substrate that will overcome these issues.

Disclosed herein is a method for coating porous metal members (e.g., impellers; spargers) with one or more layers of metal, ceramic, or polymeric particles. The method comprises of disposing particles in a solution and applying the solution on a porous metal substrate. The porous metal substrate with the particles disposed thereon is subjected to a drying process to remove solvents. The metal particles forming a porous layer after drying can then be sintered or diffusion bonded to the porous metal member. The porous coating can have a different pore size and/or chemistry than the pores and base composition of the porous metal substrate.

The porous metal substrate can comprise a network of interconnected pores. Some suitable metal substrates include substrates that comprise of iron, aluminum, titanium, nickel, chromium, cobalt, copper, gallium, gold, silver, platinum, palladium, chromium, manganese, magnesium, silicon, vanadium, zinc, zirconium, or alloys thereof. A suitable alloy for use in the metal substrate is 316 L stainless steel. Non-metallic elements may also be added to the aforementioned metals for improved properties (mechanical strength, formability, etc.) Such non-metals may include, for example, carbon, phosphorus, boron, or the like, or a combination thereof.

Alloys can be preferred. Some suitable alloys are stainless steel, carbon steel, titanium-aluminum alloys, ferroalloys, ferroboron, ferrochrome (chromium), ferromagnesium, ferromanganese, ferromolybdenum, ferronickel, ferrophosphorus, ferrotitanium, ferrovanadium, ferrosilicon, Al—Li (aluminum, lithium, sometimes mercury), Alnico (aluminum, nickel, copper), Duralumin (copper, aluminum), Magnalium (aluminum, 5% magnesium), Magnox (magnesium oxide, aluminum), Nambe (aluminum plus seven other unspecified metals), Silumin (aluminum, silicon), Billon (copper, silver), Brass (copper, zinc), Calamine brass (copper, zinc), Chinese silver (copper, zinc), Dutch metal (copper, zinc), Gilding metal (copper, zinc), Muntz metal (copper, zinc), Pinchbeck (copper, zinc), Prince's metal (copper, zinc), Tombac (copper, zinc), Bronze (copper, tin, aluminum, or any other element), Alumel (nickel, manganese, aluminum, silicon), Chromel (nickel, chromium), Cupronickel (nickel, bronze, copper), German silver (nickel, copper, zinc), Hastelloy (nickel, molybdenum, chromium, sometimes tungsten), Inconel (nickel, chromium, iron), Monel metal (copper, nickel, iron, manganese), Mu-metal (nickel, iron), Ni—C(nickel, carbon), Nichrome (chromium, iron, nickel), Nicrosil (nickel, chromium, silicon, magnesium), Nisil (nickel, silicon), Nitinol (nickel, titanium, shape memory alloy), or the like, or a combination thereof.

As noted above, the porous substrate can comprise a network of interconnected pores. This structure can be made via powder metallurgy processes. One method of manufacture includes the dispensing of powder into a die, consolidation of said powder within the die to form a green body, and heat treatment of the green body to form a diffusion bonded structure comprising interconnected pore channels. Another method involves the dispensing of powder on to a roll, which is then compacted via a secondary roll to produce a thin green body, which also experiences aforementioned diffusion bonding process. The bonded sheet is then rolled and welded to form a porous metal tube. For both methods, the diffusion bonding process (to produce the diffusion bonded structure) takes place at temperatures of 1500 to 2500° F. in the presence of a vacuum, hydrogen, argon, nitrogen, oxygen, or the like, or a combination thereof. For both methods, the use of the word "green" refers to the step in the manufacturing process and not the color of the material. In addition, fugitive materials such as poly(vinyl alcohol) or poly(methylmethacrylate) can be included along with the metal powder to help shape pores of specific sizes.

The porous metal substrate (e.g., to fabricate a porous impeller or a porous sparger) formed by this process can have an average pore size of 0.1 to 100 micrometers depending on the desired output and manufacturing parameters. Some preferred embodiments are characterized by an average pore size between 0.5 to 2 micrometers.

The coating solution used to form the porous coated layer on the metal substrate generally comprises a particulate material with a mean particle size of 50 nanometers to 60 micrometers, a solvent, a dispersant such as an anionic polymer, and a binder to assist with drying such as a polymeric material or a co-solvent. The coating solution may exist in the form of a slurry or in the form of a solution (where solids such as the particulate material, the dispersant and the binder are dissolved in the solvent). For the particulate material, generally a metallic particle is used, such as the alloy 316L stainless steel. However, a non-metallic material, such as titanium oxide and polyether ether ketone can also be used. In other words, metallic or nonmetallic coating particles may be used to form the porous coated layer.

The particulate may be but is not limited to the same material as the substrate. The material selection can be constrained by being able to produce diffusion bonding between the particulate and the substrate (e.g., porous metal substrate). The porosity of the coating layer can be determined by the size of the particulate material, and as such, there is a variety of ranges used to produce specific pore sizes in the coating. Some preferred ranges of mean particle sizes for the particulate material include 50 to 100 nanometers, 100 to 500 nanometers, 500 nanometers to 1 micrometer, 1 micrometer up to 10 micrometers and 30 micrometers to 60 micrometers. To apply the particulate to the surface of the sparger, a solvent can be used to suspend the particles to form a slurry. The solvent does not dissolve the coating material to a meaningful degree but exists to fluidize the particulate. Some preferred solvents include water, glycerol, and tetrahydrofuran (THF). A list of different solvents is provided below.

Liquid aprotic polar solvents such as propylene carbonate, ethylene carbonate, butyrolactone, acetonitrile, benzonitrile, nitromethane, nitrobenzene, sulfolane, dimethylformamide, N-methylpyrrolidone, or the like, or combinations thereof are generally desirable for suspending the particulate in a liquid solution. Polar protic solvents such as, water, glycerol, glycerin, methanol, acetonitrile, nitromethane, ethanol, propanol, isopropanol, butanol, or the like, or combinations thereof may be used. Other non-polar solvents such a benzene, toluene, methylene chloride, carbon tetrachloride, hexane, diethyl ether, tetrahydrofuran, or the like, or combinations thereof may also be used as a liquid to suspend the particles to form a coating solution.

Stabilizing agents in the form of surfactants or polymeric binders may be present in the coating solution to promote the stability of the particles in the solution. These agents can serve to prevent agglomeration and to prevent flocculation of the particles. Polymeric stabilizing agents may be selected depending upon the chemistry of the solvent. Suitable agents include polyacrylic acids, polyacrylics, polyacrylates, polymethacrylates, polymethylmethacrylates, polysiloxanes, polyolefins, or the like, or a combination thereof. The stabilizers can be present in the coating solution in an amount of 0.5 to 2 weight percent based on the weight of the coating solution.

The porous coating layer formed via the application of the coating solution can have a pore size similar to or different from the substrate. Generally, the coated pores are smaller than the substrate pores. In an embodiment, the pores in the coating layer have a mean pore size close to 50 nanometers. The range in pore sizes span from 50 nanometers to 10 micrometers, with a preferred range from 50 nanometers to 500 nanometers. The porosity of the coating can range from 40 to 90% dense, with the preferred range between 60 to 70% dense. The thickness of the coating can be 20 to 250 microns, preferably 20 to 60 microns, and can be applied in 1 to 5 layers, for example.

The coating layer generally does not penetrate into the substrate. A portion of the internal pore channel walls may be coated as a result from the process. The depth of penetration can be on the order of 10 to 30 micrometers, but is generally less than 10 micrometers.

In an embodiment, the metal particles are mixed with a suitable solvent to form a slurry. The weight percent is based on the total weight of the metal particles and the solvent. The porous metal particles can be present in the coating solution in an amount of 1 to 10 weight percent, based on a total weight of the coating solution. In a preferred embodiment, the porous metal particles are present in the coating solution in an amount of 2.5 to 4 weight percent, based on a total weight of the coating solution.

In an embodiment, the porous coating layer may have a multimodal pore size distribution. Multimodal size distributions may include bimodal pore size distributions, trimodal pore size distributions, and so on.

In an embodiment, the porous coating layer may comprise two or more layers wherein each layer has a different average pore size. For example, a first coating layer disposed on the substrate and in contact with it may have a first average pore size while a second coating layer disposed on the first coating layer and in contact with it may have a second average pore size, where the second average pore size is larger than the first average pore size or vice versa. In this manner, the porous coating layer may comprise a plurality of layers with each layer having a different average pore size from the layer adjacent to it in order to tailor filtration performance of the coated article.

In an embodiment, the porous coating layer may comprise a plurality of layers with a gradient in pore sizes, with the layer having the largest average pore sizes being closest to the substrate and the layer having the smallest average pore sizes being farthest from the substrate. In another embodiment, the porous coating layer may comprise a plurality of layers with a gradient in pore sizes, with the layer having the largest average pore sizes being farthest from the substrate and the layer having the smallest average pore sizes being closest to the substrate. The gradient in pore sizes may be a linear gradient, a curvilinear gradient, a step gradient, or a combination thereof.

In an embodiment, the porous coating layer may comprise a plurality of layers wherein each layer comprises a material having a different chemical composition from an adjacent layer or from any other layer in the porous coating layer. For example, a first layer in the porous coating layer may comprise a first metal, polymer or a ceramic while a second adjacent layer may comprise a second metal, ceramic or a polymer that is different from the first metal, polymer or the ceramic.

In an embodiment, in a manner of coating the metal substrate, a pre-wetted (in de-ionized water) porous metal substrate is dip-coated in the slurry or solution, using an optimum immersion time, and lift-up speed. The as-formed coating will be dried at room temperature and atmospheric pressure, and thereafter will be at a temperature between 1400° F. and 2250° F. in an inert atmosphere to prevent oxidation of the underlying porous metal substrate. Inert atmosphere can be preferably created by introducing an inert (e.g., $N_2$) or noble (e.g., Ar) gas into furnace hot-zone and maintaining either a positive or a partial pressure of the selected gas. In addition, a vacuum less than 1000 mTorr or a reducing gas (e.g., $H_2$) can be used.

In another embodiment, in another method of coating the porous metal substrate, the porous metal particles are suspended in a solution of isopropyl alcohol, toluene, water, glycerol, or combination thereof. Additives such as poly (acrylic acid) can be used as stabilizing agents as well. The metal particles are in solution at a concentration between 10 to 30 g/L. The particulate is kept in solution via direct agitation with a mixer between speeds of 100 to 1,000 RPM depending on particle size. Typically, 300 RPM is used. The porous metal substrate, fixtured in a way to seal off surfaces that are not to be coated, is submerged into this slurry solution. A pressure gradient is applied to pull the slurry through the porous substrate in a way to cause deposition of the metal particles on to the surface of the substrate. This gradient can be generated either by a positive pressure outside of the substrate or a negative pressure from within/behind the substrate.

In an embodiment, the solution is pulled through a porous tube at a differential pressure of −15 (minus 15) inches of Hg. The coating solution, once coating the surface of the media, is then allowed to dry. Drying can depend on the specific coating formulation—it can range from exposure to air at 115° C. for 2 up to 6 hours to drying overnight at ambient conditions. In one embodiment, the substrate is dried overnight then followed by exposure to nitrogen gas at 90° C. for 4 hours.

The coating solution can then be sinter-bonded to the substrate. In one embodiment that employs 316L stainless steel powder with a mean particle size between 60 to 80 nanometers, the coating particulates are sinter bonded to the substrate at a temperature of up to 900° C. for up to 4 hours dwell time. Typically, temperatures of 700 to 800° C. for a dwell time of 3 to 4 hours are used. The coating thickness is between 20 to 200 micrometers, preferably between 20 to 30 micrometers, may or may not contain cracks, and can be applied in 1 to 5 layers.

The resultant porous structure of the coating can be variable depending on the formulation. In one embodiment, the porous coating reaches a bubble point pressure of 16 in. Hg, indicative of a 50 to 100 nanometer mean pore size. One advantage of this coating over traditional coated ceramic media is the ability to use a lower gas pressure in application. In addition, metal substrates are less prone to fracture as compared to ceramic media. They are also stronger than plastic media and can hold up to higher pressures and/or temperatures without deforming.

Example

This example demonstrates the formation of a coating of the porous metal particles on the porous substrate. As shown in FIG. 20, a pump 90 and vacuum flask 92 capable of producing a vacuum is connected to the porous metal substrate 94 to create air flow through the metal substrate 94 from the exterior surface to the interior. This is depicted in FIG. 20. The porous metal substrate 94 is immersed into an agitated liquid/powder suspension (the coating solution) in a tank 96 and the filtration capabilities of the porous metal substrate 94 is used to allow the liquid phase (the coating solution that contains the porous metal particles) to pass through the porous metal substrate 94 and capture the porous metal particles in the porous metal substrate surface.

The porous metal substrate 94 is then removed from the tank 96 having the coating solution and the differential vacuum level is maintained in order to draw the remaining liquid from the porous metal substrate 94 to allow the porous metal particles to remain on the surface (filter cake) of the porous metal substrate to dry. The particles are then sinter bonded to form the coating on the porous metal substrate in a reducing atmosphere furnace to permanently bond the porous metal particle coasting onto the surface of the porous metal substrate.

The coating thickness can be controlled by time and flow rate when immersed into the coating solution and by the particulate concentration of the coating solution. Multiple coatings may be applied to provide thicker uniform coatings without cracks if needed. The pore size of the coating can be controlled by the sinter bonding temperatures and the average size of the particulate in coating solution used to apply the coatings.

In exemplary embodiments, a fabricated porous sparger (or fabricated porous impeller/blade) shape according to the present disclosure can be of nearly any shape and size. It is noted that an example sparger design can be a porous tube attached to a compression or NPT fitting that is located near the bottom of a process tank such as a bioreactor vessel 210. As discussed above, the example tank 210 can have a mechanical mixing impeller (e.g., porous impellers 212, 1212A, 1212B, etc., discussed above) to mix a product in the tank 210 for a more uniform distribution and temperature and provide fluid flow over the fabricated porous sparger to assist is the sparging process. The fabricated porous sparger can be a tube design or any design such as plate, ring, tree or numerous other configurations.

Exemplary fabricated porous spargers of the present disclosure can be used for any sparging applications that require gas/liquid mass transfer (e.g., bio-reactors, fermentation tanks, oxygenation, oxygen stripping). Exemplary fabricated porous impellers of the present disclosure (e.g., porous impellers 212, 1212A, 1212B, etc., discussed above) can also be used for various filtration applications, as discussed in detail above.

In example embodiments, the fabricated spargers of the present disclosure can be integrated with the mixing impellers (e.g., porous impellers 212, 1212A, 1212B, etc., discussed above), where one can fabricate porous impellers and/or blades according to the present disclosure, and attach them to a hollow shaft that provides the mechanical rotation for mixing and provide a fluid path for gas through the integrated porous sparger member. The porous blades can be coated with the nano particles as described above. This variation provides mechanical mixing and sparging in one assembly (e.g., assembly 200), and the mechanical rotation of the porous blades allows for stripping of bubbles from the sparger sooner making the bubbles smaller and more efficient for gas transfer to the liquid. It can also help to prevent plugging/clogging of the pores in the spargers and impellers of the present disclosure.

As such, the present disclosure also provides for at least one fabricated porous sparging member (94) mounted with respect to the shaft (e.g., 204B; etc.), and wherein at least a portion of the shaft provides a fluid path for fluid or gas through the at least one porous sparging member (94). In some embodiments, it is noted that at least one porous sparging member (94) can a porous tube, plate, ring or tree.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. A "combination thereof" is open and includes any combination comprising at least one of the listed components or properties optionally together with a like or equivalent component or property not listed.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A fluid assembly comprising:

a vessel configured to house a fluid;

a motor in operative communication with a shaft, and a first porous impeller mounted with respect to the shaft, the first porous impeller configured to be immersed in the fluid housed in the vessel so that when rotary motion from the motor is transferred to the first porous impeller, the first porous impeller moves and agitates the fluid;

wherein filtrate from the fluid can be extracted from the vessel via the first porous impeller, wherein:

the shaft includes a primary shaft and a hollow secondary shaft; the filtrate can be extracted from the vessel without detaching the primary shaft from the hollow secondary shaft;

the primary shaft is in operative communication with the hollow secondary shaft via an idling shaft; and the primary shaft, the hollow secondary shaft and the idling shaft are in rotary communication with each other via gears or a belt drive.

2. The fluid assembly of claim 1, wherein the vessel is a bioreactor.

3. The fluid assembly of claim 1, wherein the filtrate can be extracted from the vessel without changing speed or position of the first porous impeller.

4. The fluid assembly of claim 1, wherein the first porous impeller is a first micro-porous impeller; and wherein the first micro-porous impeller has pores having a range of pores sizes of from about 50 nanometers to about 60 micrometers.

5. The fluid assembly of claim 1, wherein the first porous impeller is in fluid communication with a hollow portion of the shaft, and the filtrate can be extracted from the vessel via the hollow portion of the shaft; and wherein the hollow portion of the shaft discharges the filtrate to a discharge conduit.

6. The fluid assembly of claim 5 further comprising a head plate at a top portion of the vessel; and wherein at least a portion of the discharge conduit is positioned below the head plate.

7. The fluid assembly of claim 1, wherein the primary shaft is laterally offset from the hollow secondary shaft.

8. The fluid assembly of claim 1, wherein an axis of the primary shaft is concentric with an axis of the hollow secondary shaft.

9. The fluid assembly of claim 1, wherein the primary shaft can detachably communicate with the hollow secondary shaft.

10. The fluid assembly of claim 1, wherein the motor can be moved laterally to engage the primary shaft with the hollow secondary shaft.

11. The fluid assembly of claim 1, wherein the hollow secondary shaft is in fluid communication with the porous impeller and discharges fluid to a discharge conduit.

12. The fluid assembly of claim 11, wherein the discharge conduit contacts the hollow secondary shaft via a bearing which permits the hollow secondary shaft to rotate while permitting the discharge conduit to remain stationary.

13. The fluid assembly of claim 11, wherein the discharge conduit contacts the hollow secondary shaft via a seal which prevents fluid leakage.

14. The fluid assembly of claim 13 further comprising a head plate at a top portion of the vessel; and wherein the seal is positioned below the head plate.

15. The fluid assembly of claim 11, further comprising a central hollow region for supporting the hollow secondary shaft, the central hollow region comprising: (i) a plurality of adapter plates with o-ring seals for non-rotating surfaces and lip seals for the rotating hollow secondary shaft to seal to the adapter plates; (ii) a central region situated between the adapter plates that is in operative communication with an exit port in the hollow secondary shaft, the central region being operative to receive the filtrate and to discharge the filtrate to the discharge conduit; and (iii) at least one connector disposed on at least one side of one of the adapter plates to attach to the vessel.

16. The fluid assembly of claim 1, wherein the hollow secondary shaft comprises an outlet port for filtrate removal from the vessel, the outlet port in fluid communication with a discharge conduit.

17. The fluid assembly of claim 1, wherein the shaft includes a hollow primary shaft and a hollow secondary shaft.

18. The fluid assembly of claim 17, wherein the hollow primary shaft comprises an outlet port for filtrate removal from the vessel, the outlet port in fluid communication with a discharge conduit.

19. The fluid assembly of claim 17, wherein an axis of the hollow primary shaft is concentric with an axis of the hollow secondary shaft.

20. The fluid assembly of claim 17, wherein the hollow secondary shaft is in fluid communication with the first porous impeller and discharges filtrate to a discharge conduit that contacts the hollow primary shaft.

21. The fluid assembly of claim 20, wherein the discharge conduit contacts the hollow primary shaft via a bearing which permits the hollow primary shaft to rotate while permitting the discharge conduit to remain stationary.

22. The fluid assembly of claim 20, wherein the discharge conduit contacts the hollow primary shaft via a seal which prevents fluid leakage.

23. The fluid assembly of claim 1, wherein the first porous impeller includes an outer surface, the outer surface substantially porous throughout the outer surface of the first porous impeller.

24. The fluid assembly of claim 1, wherein the first porous impeller includes an outer surface, the outer surface porous at pre-determined locations of the outer surface of the first porous impeller.

25. The fluid assembly of claim 1, wherein the first porous impeller is fabricated from at least one of metals, polymers or ceramics.

26. The fluid assembly of claim 1 further comprising a second impeller mounted with respect to the shaft, and wherein the second impeller is porous or non-porous.

27. The fluid assembly of claim 1, further comprising at least one porous sparging member mounted with respect to the shaft; and wherein at least a portion of the shaft provides a fluid path for fluid or gas through the at least one porous sparging member; and wherein the at least one porous sparging member is a porous tube, plate, ring or tree.

28. The fluid assembly of claim 27, wherein the first porous impeller or the at least one porous sparging member is fabricated by:

disposing a porous metal substrate in a coating solution that comprises metallic or nonmetallic coating particles;

subjecting the porous metal substrate to a positive pressure to drive the coating solution through the porous metal substrate; or alternatively subjecting the porous metal substrate to a negative pressure to drive the coating solution through the porous metal substrate; or alternatively disposing the metallic or nonmetallic coating particles on a surface of the porous metal substrate via a process of dipping the porous metal substrate into the coating solution while removing the solvent at a controlled rate to deposit a coating layer on the porous metal substrate to form the first porous impeller or the at least one porous sparging member.

29. The fluid assembly of claim 1, wherein the first porous impeller comprises a first blade and a second blade.

30. The fluid assembly of claim 29, wherein the first and second blades of the first porous impeller are angled relative to a horizontal plane of a bottom surface of the shaft.

31. The fluid assembly of claim 30 further comprising a second porous impeller mounted with respect to the shaft, the second porous impeller comprising a first blade and a second blade; wherein filtrate from the fluid can be extracted from the vessel via the second porous impeller.

32. The fluid assembly of claim 31, wherein the first and second blades of the second porous impeller are angled relative to the horizontal plane of the bottom surface of the shaft.

33. The fluid assembly of claim 32, wherein the first and second blades of the second porous impeller are angled at a different and lower angle relative to the horizontal plane of the bottom surface of the shaft than the angle of the first and second blades of the first porous impeller.

34. The fluid assembly of claim 31, wherein the first and second blades of the second porous impeller are co-planar relative to the horizontal plane of the bottom surface of the shaft.

35. The fluid assembly of claim 29, wherein the first and second blades of the first porous impeller are angled from about 30° to about 60° relative to a horizontal plane of a bottom surface of the shaft.

36. The fluid assembly of claim 1, wherein the first porous impeller comprises a single contiguous body.

37. The fluid assembly of claim 36, wherein the first porous impeller is a disk or a wheel.

38. The fluid assembly of claim 36, wherein a porous region of the first porous impeller is spaced a distance from the shaft.

39. The fluid assembly of claim 36, further comprising a second impeller mounted with respect to the shaft, the second impeller comprising a first blade and a second blade, the first and second blades of the second porous impeller angled relative to the horizontal plane of the bottom surface of the shaft.

40. The fluid assembly of claim 39, wherein the first porous impeller is co-planar relative to the horizontal plane of the bottom surface of the shaft.

41. A fluid assembly comprising:

a vessel configured to house a fluid; a motor in operative communication with a shaft, and a first porous impeller mounted with respect to the shaft, the first porous impeller configured to be immersed in the fluid housed in the vessel so that when rotary motion from the motor is transferred to the first porous impeller, the first porous impeller moves and agitates the fluid, wherein filtrate from the fluid can be extracted from the vessel via the first porous impeller; and a housing surrounding at least a portion of the first porous impeller, the housing configured to create pressure on the first porous impeller to promote fluid flow through the first porous impeller, wherein the housing is an inverted cup housing; and wherein a top surface of the housing has at least one opening.

42. A fluid assembly comprising:

a vessel configured to house a fluid; a motor in operative communication with a shaft, and a first porous impeller mounted with respect to the shaft, the first porous impeller configured to be immersed in the fluid housed in the vessel so that when rotary motion from the motor is transferred to the first porous impeller, the first porous impeller moves and agitates the fluid, wherein filtrate from the fluid can be extracted from the vessel via the first porous impeller; and wherein:

the shaft includes an upper manifold and a lower manifold, the upper manifold mounted with respect to the lower manifold by a first side member and a second side member, and the first porous impeller mounted with respect to the first and second side members; and the first and second side members comprise flexible ropes.

43. The fluid assembly of claim 42, further comprising a second porous impeller mounted with respect to the first and second side members.

44. The fluid assembly of claim 43, wherein the second porous impeller is configured to be positioned at a different elevational position than the first porous impeller within the vessel.

45. The fluid assembly of claim 42, wherein a first exterior edge of the first porous impeller is connected to the first side member, and a second exterior edge of the first porous impeller is connected to the second side member.

46. The fluid assembly of claim 42, wherein filtrate from the fluid can be extracted from the vessel via the first porous impeller, the first and second side members and the lower manifold.

47. The fluid assembly of claim 46, wherein the lower manifold is mounted with respect to a rotary fluid port.

* * * * *